US008710027B2

(12) United States Patent
Philippov et al.

(10) Patent No.: US 8,710,027 B2
(45) Date of Patent: Apr. 29, 2014

(54) METHOD OF USING NUTRITIONAL COMPOUNDS DIHYDROQUERCETIN (TAXIFOLIN) AND ARABINOGALACTAN IN COMBINATION WITH DIHYDROQUERCETIN (TAXIFOLIN) TO REDUCE AND CONTROL CARDIOMETABOLIC RISK FACTORS ASSOCIATED WITH METABOLIC SYNDROME AND HYPERCHOLESTEROLEMIA

(75) Inventors: Sergey V. Philippov, Moscow (RU); Igor M. Bogorodov, Moscow (RU)

(73) Assignee: Flavitpure, Inc., Cheyenne, WY (US)

( * ) Notice: Subject to any disclaimer, the term of this patent is extended or adjusted under 35 U.S.C. 154(b) by 0 days.

(21) Appl. No.: 13/443,023

(22) Filed: Apr. 10, 2012

(65) Prior Publication Data
US 2013/0267477 A1  Oct. 10, 2013

(51) Int. Cl.
*A61K 31/715* (2006.01)
*A61K 31/352* (2006.01)

(52) U.S. Cl.
CPC ............ *A61K 31/352* (2013.01); *A61K 31/715* (2013.01)
USPC .......................................................... 514/54

(58) Field of Classification Search
CPC ........................... A61K 31/352; A61K 31/715
USPC ............................................................ 514/54
See application file for complete search history.

(56) References Cited

U.S. PATENT DOCUMENTS 5,614,501 A * 3/1997 Richards ......................... 514/22
2005/0137253 A1* 6/2005 Phinney et al. ............... 514/458

OTHER PUBLICATIONS

Theriault et al. Modulation of hepatic lipoprotein synthesis and secretion by taxifolin, a plant flavonoid. J Lipid Res 41:1969-1979, 2000.*
Cornier et al. The metabolic syndrome. Endocrine Rev 29:777-822, 2008.*

* cited by examiner

*Primary Examiner* — Brandon Fetterolf
*Assistant Examiner* — Yih-Horng Shiao
(74) *Attorney, Agent, or Firm* — Anna Vishev

(57) ABSTRACT

The method of using nutritional compounds including Dihydroquercetin (taxifolin), Arabinogalactan and Arabinogalactan combined with Dihydroquercetin (taxifolin) to reduce and control cardiometabolic risk factors, associated with metabolic syndrome and hypercholesterolemia in a mammal, specifically a human, resulting in the enhancement of metabolism, reduced control levels of cholesterol and triglycerides, reduced oxidative damage in humans and other health benefits.

11 Claims, 6 Drawing Sheets

FIG. 8

| Sample | FRAP [a] | TEAC [b] | Deoxyribose [c] |
|---|---|---|---|
| Dihydroquercetin (PUREDHQ)™ | 180.73 ± 11.05 | 462.99 ± 28.56 | 52.29 ± 3.03 |
| Larch Arabinogalactan consisting with Dihydroquercetin (PURELAG™5) | 41.91 ± 0.82 | 51.62 ± 5.59 | 35.46 ± 2.08 |

Values expressed as mean value ± standard deviation (n=3)

[a] mmol Fe (II)/L FW

[b] mmol Trolox/L FW

[c] IC50 value

METHOD OF USING NUTRITIONAL COMPOUNDS DIHYDROQUERCETIN (TAXIFOLIN) AND ARABINOGALACTAN IN COMBINATION WITH DIHYDROQUERCETIN (TAXIFOLIN) TO REDUCE AND CONTROL CARDIOMETABOLIC RISK FACTORS ASSOCIATED WITH METABOLIC SYNDROME AND HYPERCHOLESTEROLEMIA

REFERENCES

Fito M, Guxens M, Corella D, Saez G, Estruch R, de la Torre R, Frances F, Cabezas C, Lopez-Sabater Mdel C, Marrugat J, Garcia-Arellano A, Aros F, Ruiz-Gutierrez V, Ros E, Salas-Salvado J, Fiol M, Sola R, Covas M I. (2007). Effect of a traditional Mediterranean diet on lipoprotein oxidation: a randomized controlled trial. *Arch. Intern. Med.,* 167:1195-1203.

Mitrou P N, Kipnis V, Thiebaut A C, Reedy J, Subar A F, Wirfalt E, Flood A, Mouw T, Hollenbeck A R, Leitzmann M F, Schatzkin A. (2007). Mediterranean dietary pattern and prediction of all-cause mortality in a US population: results from the NIH-AARP Diet and Health Study. *Arch. Intern. Med.,* 167:2461-2468.

O'Keefe J H, Bell D S. (2007). Postprandial hyperglycemia/hyperlipidemia (postprandial dysmetabolism) is a cardiovascular risk factor. *Am. J. Cardiol.,* 100:899-904.

Grundy, Nat. Rev. Drug Disc. 5 (2006): 295-309.

Eckel R H, Grundy S M. Zimmet P Z: The metabolic syndrome. Lancet 2005, 365:1415-1428.

Moller D E, Kaufman K D: Metabolic syndrome: a clinical and molecular perspective. Annu Rev Med 2005, 56:45-62.

Ford E S: Prevalence of the metabolic syndrome defined by the International Diabetes Federation among adults in the U.S. Diabetes Care 2005, 28:2745-2749.

Batsis J A, Nieto-Martinez R E, Lopez-Jimenez F: Metabolic syndrome: from global epidemiology to individualized medicine. Clin Pharmacol Ther 2007, 82:509-524.

Day C: Metabolic syndrome, or What you will: definitions and epidemiology. Diab Vasc Dis Res 2007, 4:32-38.

Forsythe C E, Phinney S D, Fernandez M L, Quann E E, Wood R J, Bibus D M, Kraemer W J, Feinman R D, Volek J S: Comparison of low fat and low carbohydrate diets on circulating fatty acid composition and markers of inflammation. Lipids 2008, 43:65-77.

Volek J S, Feinman R D: Carbohydrate restriction improves the features of Metabolic Syndrome. Metabolic Syndrome may be defined by the response to carbohydrate restriction. Nutr Metab (Lond) 2005, 2:31.

Volek J S, Fernandez M L, Feinman R D, Phinney S D: Dietary carbohydrate restriction induces a unique metabolic state positively affecting atherogenic dyslipidemia, fatty acid partitioning, and metabolic syndrome. Prog Lipid Res 2008, 47:307-318.

Riccardi G, Giacco R, Rivellese A A: Dietary fat, insulin sensitivity and the metabolic syndrome. Clin Nutr 2004, 23:447-456.

Dandona P, Aljada A, Bandyopadhyay A: Inflammation: the link between insulin resistance, obesity and diabetes. Trends Immunol 2004, 25:4-7.

McGarry J D: Banting lecture 2001: dysregulation of fatty acid metabolism in the etiology of type 2 diabetes. Diabetes 2002, 51:7-18.

Slawik M, Vidal-Puig A J: Lipotoxicity, overnutrition and energy metabolism in aging. Ageing Res Rev 2006, 5:144-164.

Boden G, Chen X, Rosner J, Barton M: Effects of a 48-h fat infusion on insulin secretion and glucose utilization. Diabetes 1995, 44:1239-1242.

Brechtel K, Dahl D B, Machann J, Bachmann O P, Wenzel I, Maier T, Claussen C D, Haring H U, Jacob S, Schick F: Fast elevation of the intramyocellular lipid content in the presence of circulating free fatty acids and hyperinsulinemia: a dynamic 1H-MRS study. Magn Reson Med 2001, 45:179-183.

Kelley D E, Mintun M A, Watkins S C, Simoneau J A, Jadali F, Fredrickson A, Beattie J, Theriault R: The effect of non-insulin-dependent diabetes mellitus and obesity on glucose transport and phosphorylation in skeletal muscle. J Clin Invest 1996, 97:2705-2713.

Roden M, Price T B, Perseghin G, Petersen K F, Rothman D L, Cline G W, Shulman G I: Mechanism of free fatty acid-induced insulin resistance in humans. J Clin Invest 1996, 97:2859-2865.

Permana P A, Menge C, Reaven P D: Macrophage-secreted factors induce adipocyte inflammation and insulin resistance. Biochem Biophys Res Commun 2006, 341:507-514.

Weisberg S P, McCann D, Desai M, Rosenbaum M, Leibel R L, Ferrante A W Jr: Obesity is associated with macrophage accumulation in adipose tissue. J Clin Invest 2003, 112:1796-1808.

Patiag D, Gray S, Idris I, Donnelly R: Effects of tumour necrosis factor-alpha and inhibition of protein kinase C on glucose uptake in L6 myoblasts. Clin Sci (Lond) 2000, 99:303-307.

Plomgaard P, Bouzakri K, Krogh-Madsen R, Mittendorfer B, Zierath J R, Pedersen B K: Tumor necrosis factor-alpha induces skeletal muscle insulin resistance in healthy human subjects via inhibition of Akt substrate 160 phosphorylation. Diabetes 2005, 54:2939-2945.

Ranganathan S, Davidson MB: Effect of tumor necrosis factoralpha on basal and insulin-stimulated glucose transport in cultured muscle and fat cells. Metabolism 1996, 45:1089-1094.

Assmann G, Guerra R, Fox G Cullen P, Schulte H, Willett D, Grundy S M. Harmonizing the definition of the metabolic syndrome: comparison of the criteria of the Adult Treatment Panel III and International Diabetes Federation in United States American and European populations. Am. J. Cardiol. 2007; 99: 541-8.

Grundy S M, Cleeman J I, Daniels S R, Donato K A, Eckel R H, Franklin B A, Gordon D J, Krauss R M, Savage P J, Smith S C, Spertus J A, Costa F. Diagnosis and management of the metabolic syndrome: an American Heart Association/National Heart, Lung, and Blood Institute Scientific Statement. Circulation 2005; 112: 2735-52.

Groop L. Genetics of the metabolic syndrome. Br. J. Nutr. 2000; 83 (Suppl 1): S39-48.

Szabo D E, Edelenyi F, Goumidi L, Bertraiss S, Philips C, MacManus R, Roche H, Planells R, Lairon D. Prediction of the metabolic syndrome status based on dietary and genetic parameters, using Random Forest. Genes Nutr. 2008; 3: 173-6.

Gami A S, Witt B J, Howard D E, Erwin P J, Gami L A, Somers V K, Montori V M. Metabolic syndrome and risk of incident cardiovascular events and death: a systematic review and meta-analysis of longitudinal studies. J. Am. Coll. Cardiol. 2007; 49: 403-13.

Katzmarzyk P T, Church T S, Blair S N. Cardiorespiratory fitness attenuates the effects of the metabolic syndrome on all-cause and cardiovascular disease mortality in men. Arc. Intern. Med. 2004; 164:1092-97.

Lakka H M, Laaksonen D E, Lakka T A, Niskanen L K, Kumpusalo E, Tuomolehto J, Salonen J T. The metabolic syndrome and total and cardiovascular disease mortality in middle-aged men. JAMA. 2002; 288:2709-16.

De Vriese A S, Verbeuren T J, van d, V, Lameire N H, Vanhoutte P M: Endothelial dysfunction in diabetes. Br J Pharmacol 2000, 130:963-974.

Feldt-Rasmussen B: Microalbuminuria, endothelial dysfunction and cardiovascular risk. *Diabetes Metab* 2000, 26(Suppl 4):64-66.

Ribau J C, Hadcock S J, Teoh K, DeReske M, Richardson M: Endothelial adhesion molecule expression is enhanced in the aorta and internal mammary artery of diabetic patients. *J Surg Res* 1999, 85:225-233.

Rask-Madsen C, Ihlemann N, Krarup T, Christiansen E, Kober L, Nervil KC, Torp-Pedersen C: Insulin therapy improves insulin-stimulated endothelial function in patients with type 2 diabetes and ischemic heart disease. *Diabetes* 2001, 50:2611-2618.

Rasmussen L M, Ledet T: Aortic collagen alterations in human diabetes mellitus. Changes in basement membrane collagen content and in the susceptibility of total collagen to cyanogen bromide solubilisation. *Diabetologia* 1993,36:445-453.

Heickendorff L, Ledet T, Rasmussen L M: Glycosaminoglycans in the human aorta in diabetes mellitus: a study of tunica media from areas with and without atherosclerotic plaque. Diabetologia 1994, 37:286-292.

Olesen P, Ledet T, Rasmussen L M: Arterial osteoprotegerin: increased amounts in diabetes and modifiable synthesis from vascular smooth muscle cells by insulin and TNF-alpha. *Diabetologia* 2005,48:561-568.

Chung A W, Booth A D, Rose C. Thompson C R, Levin A, van B C: Increased matrix metalloproteinase 2 activity in the human internal mammary artery is associated with ageing, hypertension, diabetes and kidney dysfunction. *J Vasc Res* 2008,45:357-362.

Sims T J, Rasmussen L M, Oxlund H, Bailey A J: The role of glycation cross-links in diabetic vascular stiffening. Diabetologia 1996,39:946-95,1.

Ruiz E, Gordillo-Moscoso A, Padilla E, Redondo S, Rodriguez E, Reguillo F, Briones A M, van B C, Okon E, Tejerina T: Human vascular smooth muscle cells from diabetic patients are resistant to induced apoptosis due to high Bcl-2 expression. Diabetes 2006, 55:1243-1251.

Neubauer B: A quantitative study of peripheral arterial calcification and glucose tolerance in elderly diabetics and non-diabetics. Diabetologia 1971, 7:409-413.

Lehto S, Niskanen L, Suhonen M, Ronnemaa T, Laakso M: Medial artery calcification. A neglected harbinger of cardiovascular complications in non-insulin-dependent diabetes mellitus. Arterioscler Thromb Vasc Biol 1996, 16:978-983.

Sista A K, O'Connell M K, Hinohara T, Oommen S S, Fenster B E, Glassford A J, Schwartz E A, Taylor C A, Reaven G M, Tsao P S: Increased aortic stiffness in the insulin-resistant Zucker fa/fa rat. *AM J Physiol Heart Circ Physiol* 2005,289:H845-H851.

Heinonen S E, Leppanen P, Kholova I, Lumivuori H, Hakkinen S K, Bosch F, Laakso M, Yla-Herttuala S: Increased atherosclerotic lesion calcification in a novel mouse model combining insulin resistance, hyperglycemia, and hypercholesterolemia. Circ Res 2007, 101:1058-1067.

Renard C B, Kramer F, Johansson F, Lamharzi N, Tannock L R, von Herrath M G, Chait A, Bornfeldt K E: Diabetes and diabetes-associated lipid abnormalities have distinct effects on initiation and progression of atherosclerotic lesions. J Clin. Invest 2004,114:659-668.

Vibe Skov, Steen Knudsen, Malene Olesen, Maria L Hansen, Lars M. Rasmussen. (2012). Global gene expression profiling displays a network of dysregulated genes in non-atherosclerotic arterial tissue from patients with type 2 diabetes. *Cardiovascular Diabetology* 2012, 11:15.

Guthrie J F, Lin B H, Frazao E: Role of food prepared away from home in the American diet, 1977-78 versus 1994-96: changes and consequences. J Nutr Educ Behav 2002, 34:140-150.

Choe E, Min D B: Chemistry of deep-fat frying oils. *J Food Sci* 2007, 72:77-86.

Cohn J S: Oxidized fat in the diet, postprandial lipaemia and cardiovascular disease. *Curr Opin Lipidol* 2002, 13:19-24.

Staprans I, Pan X M, Rapp J H, Feingold K R: The role of dietary oxidized cholesterol and oxidized fatty acids in the development of atherosclerosis. *Mol Nutr Food Res* 2005, 49:1075-1082.

Ringseis R, Eder K: Regulation of genes involved in lipid metabolism by dietary oxidized fat. Mol Nutr Food Res 2011, 1:109-121.

Staprans I, Rapp J H, Pan X M, Kim K Y, Feingold K R: Oxidized lipids in the diet are a source of oxidized lipid in chylomicrons of human serum. *Arterioscler Thromb* 1994, 14:1900-1905.

Hayam I, Cogan U, Mokady S: Dietary oxidized oil and the activity of antioxidant enzymes and lipoprotein oxidation in rats. Nutr Res 1995, 15:1037-1044.

Keller U, Brandsch C, Eder K: Supplementation of vitamins C and E increases the vitamin E status but does not prevent the formation of oxysterols in the liver of guinea pigs fed an oxidised fat. Eur J Nutr 2004, 43:353-359.

Izaki Y, Yoshikawa S, Uchiyama M: Effect of ingestion of thermally oxidized frying oil on peroxidative criteria in rats. Lipids 1984, 1.9:324-331.[10] Kok T S, Harris P G, Alexander J C: Heated canola oil and oxidative stress in rats. *Nutr Res* 1988, 8:673-684.

Liu J F, Huang C J: Tissue alpha-tocopherol retention in male rats is compromised by feeding diets containing oxidized frying oil. J Nutr 1995, 125:3071-3080.

Liu J F, Huang C J: Dietary oxidized frying oil enhances tissue alpha-tocopherol depletion and radioisotope tracer excretion in vitamin E-deficient rats. J Nutr 1996, 126:2227-2235.

Eder K, Stangl G I: Plasma thyroxine and cholesterol concentrations of miniature pigs are influenced by thermally oxidized dietary lipids. *J Nutr* 2000, 130:116-121.

Girotti A W. Lipid hydroperoxide generation, turnover, and effector action in biological systems. J Lipid Res. 1998;39: 1529-42.

Wang Y, Walsh S W. Increased superoxide generation is associated with decreased superoxide dismutase activity and mRNA expression in placental trophoblast cells in preeclampsia. Placenta. 2001;22:206-12.

Kontorshikova, K. N., Zhulina, N. I., Runova, A. A. (2007). Clinical study. Gerontological center, Medicine Academy, N. Novgorod. (in Russian language).

Gurnell et al., Journal of Clinical Endocrinology and Metabolism (88) (2003): 2412-2421.

Pew, John C., 1947. A flavanone from Douglas-fir heartwood. J. Am. Chem. Soc., 70 (9), pp 3031-3034.

E. F. Kurth, Harry J. Kiefer, and James K. Hubbard. (1948). Utilization of Douglas-fir Bark. The Timberman, Vol. 49, No. 8, pp. 130-1.

H. M. Graham, E. F. Kurth, (1949). Constituents of Extractives from Douglas Fir. Ind. Eng. Chem., 41 (2), pp 409-414.

Migita, Nobuhiko,-Nakano, Junzs, Sakai, Isamu, and Ishi, Shoichi, (1952). Japan Tech. Assoc. Pulp Paper Ind. 6:476-480.

Kurth, E. F., and Chan, F. L., (1953). "Extraction of Tannin and Dihydroquercetin from Douglas Fir Bark." J. Amer. Leather Chem. Assoc. 48(1):20-32, Abstr. Bull. Inst. Pap. Chem. 23:469.

G. M. Barton, J. A. F. Gardner. (1958). Determination of Dihydroquercetin in Douglas Fir and Western Larch Wood. Anal. Chem., 30 (2), pp 279-281.

G. V. Nair and E von Rudloff. (1959). THE CHEMICAL COMPOSITION OF THE HEARTWOOD EXTRACTIVES OF TAMARACK (*LARIX LARICINA* (DU ROI) K. K0CH)1. Can. J. Chem., Vol. 37, pp.1608-1613.

Tyukavkina, N. A., Lapteva, K. I., Larina V. A.. (1967). Extractives of *Larix dahurica*. Quantitative content of quercetin and dihydroquercetin. Chemistry of Natural Substances. Issue 5, pages 298-301.

E. E. Nifant'ev, M. P. Koroteev, G. Z. Kaziev, A. A. Uminskii, A. A. Grachev, V. M. Men'shov, Yu. E. Tsvetkov, N. E. Nifant'ev, V. K. Bel'skii, A. I. Stash. (2006). On the Problem of Identification of the Dihydroquercetin Flavonoid. ISSN 1070-3632, Russian Journal of General Chemistry, 2006, Vol. 76, No. 1, pp. 161-163. Pleiades Publishing, Inc., 2006. Original Russian Text published in Zhurnal Obshchei Khimii, 2006, Vol. 76, No. 1, pp. 164-166.

Ponder GR, Richards GN (1997a) Arabinogalactan from Western larch, Part II; a reversible order-disorder transition. J Carbohydr Chem 16:195-211.

Kara'csonyi S, Kova'cik V, Alföldi J, Kubackova' M (1984) Chemical and $^{13}$C-N.M.R. studies of an arabinogalactan from *Larix sibirica* L. Carbohydr Res 134:265-274.

Simionescu C, Sang II B, Cernatescu-Asandei A (1976) Researches in the field of chemistry and technology of larch wood pulping by magnesium bisulphite process. II. Structure of arabinogalactan from larch wood (*Larix decidua* Mill). Cellulose Chem. Technol., 10:535-545.

Odonmazig, P. Ebringerova, A. Machova, E. Alföldi J. (1994) Structural and molecular properties of arabinogalactan isolated from Mongolian larchwood (*Larix dahurica* L.). Carbohydr. Res. 252: 317-324.

Saura-Calixto. F. Antioxidant dietary fiber product: A new concept and a potential food ingredient. J. Agric. Food Chem. I 998,46,4303-4306.

Haraguchi H, Mochida Y, Sakai S, Masuda H, Tamura Y, Mizutani K, Tanaka O, Chou WH. (1996). Protection against oxidative damage by dihydroflavonols in *Engelhardtia chrysolepis*. Biosci Biotechnol Biochem., 60(6):945-8.)

Kostyuk V A, Potapovich A 1. (1998). Antiradical and chelating effects in flavonoid protection against silica-induced cell injury. Arch Biochem Biophys., 355(1):43-8.

Godley, Bernard F. and Shamsi, Farrukh Anis and Liang, Fong-Qi and Jarrett, Stuart Gordon and Davies, Sallyanne and Boulton, Michael Edwin. (2005). Blue light induces mitochondrial DNA damage and free radical production in epithelial cells. Journal of Biological Chemistry, 280 (22). pp. 21061-21066. ISSN 00219258.

Xinyu JIANG, Xiaoqing CHEN * and Yan WEI. (2009). Free Radical Scavenging Activity and Flavonoids Contents of *Polygonum orientate* Leaf, Stem and Seed Extracts. Lat. Am. J. Pharm. 28 (2): 284-7.

Iskandarov, A. I., Abdukarimov, B. A. (2009). Influence of Dihydroquercetin and ascorbic acid on the content of malon dialdehyde and metallothionein in rat's organs exposed to chronic cadmium impact. Journal Toxicological Vestnik, volume 4. Russian language version.

Yifan Chen. (2009). Antioxidants quercetin and dihydroquercetin inhibit ex vivo hemolysis but not plasma lipid peroxidation. FASEB J. 23: 966.3.

Bronnikov, G. E., Kulagina, T. P., Aripovsky, A. V. (2009). Dietary Supplementation of Old Mice with Flavonoid Dihydroquercetin Causes Recovery of Mitochondrial Enzyme Activities in Skeletal Muscles. ISSN 1990-7478, Biochemistry (Moscow) Supplement Series A: Membrane and Cell Biology. 2009, Vol. 3, No. 4, pp. 453-458. © Pleiades Publishing, Ltd. Russian language version. Original Russian Text © G. E. Bronnikov, T. P. Kulagina, A. V. Aripovsky, 2009, published in Biologicheskie Membrany, 2009, Vol. 26, No. 5, pp. 387-393. Russian language version.

Li, Y., and Jaiswal, A. K. (1994) Human antioxidant-response-element mediated regulation of type 1 AD(P)H: quinone oxidoreductase gene expression. Eur. J. Biochem., 226, 31-39, 1994.

Saet Byoul Lee, Kwang Hyun Cha, Dangaa Selenge, Amgalan Solongo, and Chu Won Nho. (2007). The Chemopreventive Effect of Taxifolin Is Exerted through ARE-Dependent Gene Regulation. Biol. Pharm. Bull., 30(6) 1074-1079.

van der L B, Bachschmid M, Spitzer V. et al. Decreased plasma and tissue levels of vitamin C in, a rat model of aging: implications for antioxidative defense. Biochem Biophys Res Commun. 2003 Apr. 4;303(2):483-7.

Potapovich A I, Kostyuk V A. Comparative study of antioxidant properties and cytoprotective activity of flavonoids. Biochemistry (Mosc.). 2003 May;68(5):514-9.

Kravchenko L V, Morozov S V, Tutel'yan V A. Effects of flavonoids on the resistance of microsomes to lipid peroxidation in vitro and ex vivo. Bull Exp Biol Med. 2003 Dec; 136(6):572-5.

Teselkin Y O, Babenkova I V, Tjukavkina N A, et al. Influence of dihydroquercetin on the lipid peroxidation of mice during postradiation period. Phytotherapy Research. 1998; 12:51.7-9.

Vasiljeva O V, Lyubitsky O B, Klebanov G I, Vladimirov Y A. Effect of the combined action of flavonoids, ascorbate and alphatocopherol on peroxidation of phospholipid liposomes induced by Fe2+ ions. Membr Cell Biol. 2000;14(1):47-56.

Kostyuk V A, Kraemer T, Sies H, Schewe T. Myeloperoxidase/nitrite-mediated lipid peroxidation of low-density lipoprotein as modulated by flavonoids. FEBS Lett. 2003 Feb. 27;537(1-3):146-50.

A. Hanneken, J. Johnson, F. -F. Lin. (2005). Preserving Vision in Glaucoma and Macular Degeneration: Neuroprotective Effects of the Flavonoids. Molecular and Experimental Medicine, pp.251-253. Published by TSRI Press®. ©Copyright 2005, The Scripps Research Institute.

Irene Crespo, María V. Garcia-Mediavilla, Mar Almar, Paquita González, María J. Tuñón, Sonia Sánchez-Campos and Javier González-Gallego. (2008). Differential effects of dietary flavonoids on reactive oxygen and nitrogen species generation and changes in antioxidant enzyme expression induced by proinflammatory cytokines in Chang Liver cells. Food and Chemical Toxicology, Volume 46, Issue 5, Pages 1555-1569.

Crespo I., Garcia-Mediavilla M. V., Almar M. et al. 2008.

Ishige K, Schubert D, Sagara Y. Flavonoids protect neuronal cells from oxidative stress by three distinct mechanisms. Free Radic Biol Med. 2001;30:433-446.

Kolhir, V. K., et. al. 1996. Antioxidant activity of a dihydroquercetin isolated from *Larix gmelinii*. Phytotherapy Research. 10(6): 478-482.

Maria Monagas, Nasiruddin Khan, Cristina Andrés-Lacueva, Mireia Urpí-Sardá, Mónica Vázquez-Agell, Rosa Maria Lamuela-Raventós and Ramón Estruch. (2009). Dihydroxylated phenolic acids derived from microbial metabolism reduce lipopolysaccharide-stimulated cytokine secretion by human peripheral blood mononuclear cells. British Journal of Nutrition, 102:201-206.

Kim, D.-H., Jung, E.-A., Sohng, I.-S., Han, J.-A., Kim, T.-H. & Han, M. J. (1998) Intestinal bacterial metabolism of flavonoids and its relation to some biological activities. Arch. Pharm. Res., 21: 17-23.

Logvinov S V, Pugachenko N V, Potapov A V, et al. Ischemia-induced changes in synaptoarchitectonics of brain cortex and their correction with ascovertin and Leuzea extract. Bull Exp Biol Med. 2001 October;132(4):1 017-20.

Plotnikov M B, Logvinov S V, Pugachenko N V, et al. Cerebroprotective effects of diquertin and ascorbic acid. Bull Exp Biol Med. 2000 November;130(11):1080-3. Plotnikov M B, Plotnikov D M, Aliev O I, et al. Hemorheological and antioxidant effects of Ascovertin in patients with sclerosis of cerebral arteries. Clin Hemorheol Microcirc. 2004;30(3-4): 449-52.

Wang Y H, Wang W Y, Chang C C, Liou K T, Sung Y J, Liao J F, Chen C F, Chang S, Hou Y C, Chou Y C, Shen Y C. (2006). Taxifolin ameliorates cerebral ischemia-reperfusion injury in rats through its anti-oxidative effect and modulation of NF-kappa B activation. J Biomed Sci., 13(1):127-41.

Chen, et al. Zhonghua Yi Xue Za Zhi, Taipei 2001 64:382-387.

Igarashi, et al. Biosci. Biotec. Biochem. 1996 60:513-515.

Mizutani, et al. Nippon Shokuhin Shinsozai Kenkuykaishi 1998 1:51-64.

Andre Theriault, Qi Wang, Stephen C. Van Iderstine, Biao Chen, Adrian A. Franke, and Khosrow Adeli. (2000). Modulation of hepatic lipoprotein synthesis and secretion by taxifolin, a plant flavonoid1. Journal of Lipid Research, Volume 41, pages 1969-1979.

Casaschi A, Rubio B K, Maiyoh G K, Theriault A G. (2004). Inhibitory activity of diacylglycerol acyltransferase (DGAT) and microsomal triglyceride transfer protein (MTP) by the flavonoid, taxifolin, in HepG2 cells: potential role in the regulation of apolipoprotein B secretion. Atherosclerosis, 176(2):247-53.

University of Hawai'i, Teresa D. Douglas. (2005). Effect of plant flavonoids on Peroxisome Proliferator-Activated Receptor (PPAR) protein expression in cell-line culture and hamster model. Ph.D dissertation.

Anderson R., Broadhurst C., Polansky M., et al. (2004). Isolation and characterization of polyphenol type-A polymers from cinnamon with insulin like biological activity. Journal of agricultural food chemistry. 52, 65-70.

Imparl-Radosevich J., Deas S., Polansky M., et al. (1998). Regulation of PTP-1 and insulin receptor kinase by fractions from cinnamon: implications for cinnamon regulation of insulin signaling. Hormone research, 50, 177-182.

Bronnikov, G. E., Kulagina, T. P., Aripovsky, A. V. (2009). Dietary Supplementation of Old Mice with Flavonoid Dihydroquercetin Causes Recovery of Mitochondrial Enzyme Activities in Skeletal Muscles. ISSN 1990-7478, Biochemistry (Moscow) Supplement Series A: Membrane and Cell Biology, 2009, Vol. 3, No. 4, pp. 453-458. © Pleiades Publishing, Ltd.

N. F. Fedosova, S. V. Alisievich, K. V. Lyadov, E. P. Romanova, I. A. Rud'ko, and A. A. Kubatiev. (2004). Mechanisms Underlying Dihydroquercetin-Mediated Regulation of Neutrophil Function in Patients with Non-Insulin-Dependent Diabetes Mellitus. Bulletin of Experimental Biology and Medicine, No. 1 2004 GENERAL PATHOLOGY AND PATHOLOGICAL PHYSIOLOGY. Translated from Byulleten' Eksperimental'noi Biologii i Meditsiny, Vol. 137, No. 2, pp. 164-167.

Haraguchi H, Ohmi I, Fukuda. A, et al. Inhibition of aldose reductase and sorbitol accumulation by astilbin and taxifolin dihydroflavonols in Engelhardtia chrysolepis. Biosci Biotechnol Biochem. 1997 April:61(4):651-4.

Haraguchi H, Ohmi I, Masuda H, et al. Inhibition of aldose reductase by dihydroflavonols in Engelhardtia chrysolepis and effects on other enzymes. Experientia. 1996 Jun. 15;52 (6):564-7.

Gupta M B, Bhalla T N, Gupta G P, Mitra C R, Bhargava K P. (1971). Anti-inflammatory activity of taxifolin. Japan J Pharmacol., 21(3):377-82.

Ivanenkov, Y A; Balakin, K V: Tkachenko, S E. (2008). New Approaches to the Treatment of Inflammatory Disease: Focus on Small-Molecule Inhibitors of Signal Transduction Pathways. Drugs in R & D, Volume 9—Issue 6—pp 397-434.

Xin-Xin Zhang, Xue-Feng Xiao, Qi Shan, Wen-Bin Hou. (2010). Recent Advance on Plant Sources. Bioactivities. Pharmacological effects and Pharmacokinetic Studies of Taxifolin. Asian Journal of Pharmacodynamics and Pharmacokinetics. 10(1):35-43.

Devi M A, Das N P. In vitro effects of natural plant polyphenols on the proliferation of normal and abnormal human lymphocytes and their secretions of interleukin-2. Cancer Lett. 1993 May 14;69(3):191-6.

Kim Y J, Choi S E, Lee M W, Lee C S. (2008). Dihydroquercetin (taxifolin) inhibits dendritic cell responses stimulated by lipopolysaccharide and lipoteichoic acid. J Pharm Pharmacol., 60(11):1465-72.

Sang Mi An, Hyo Jung Kim, Jung-Eun Kim, Yong Chool Boo. (2008). Flavonoids, taxifolin and luteolin attenuate cellular melanogenesis despite increasing tyrosinase protein levels. Phytotherapy Research, Volume 22, Issue 9, Pages 1200-1207.

Bjeldanes L F, Chang G W. Mutagenic activity of quercetin and related compounds. Science. 1977 Aug. 5;197(4303): 577-8.

Nagao M, Morita. N, Yahagi T, et al. Mutagenicities of 61 flavonoids and 11 related compounds. Environ Mutagen. 1981;3 (4):401-19.

Booth A N, Deeds F. The toxicity and metabolism of dihydroquercetin. J Am Pharm Assoc Am Pharm Assoc (Baltim.). 1958 March;47(3, Part 1):183-4.

William S. Branham, Stacey L. Dial, Carrie L. Moland, Bruce S. Hass, Robert M. Blair, Hong Fang. Leming Shi, Weida Tong, Roger G. Perkins and Daniel M. Sheehan. (2002). Phytoestrogens and Mycoestrogens Bind to the Rat Uterine Estrogen Receptor. Biochemical and Molecular Action of Nutrients, © 2002 American Society for Nutritional Sciences.

Wendy N. Jefferson, Elizabeth Padilla-Banks, George Clarkb, Retha R. Newbold. (2002). Assessing estrogenic activity of phytochemicals using transcriptional activation and immature mouse uterotrophic responses. Journal of Chromatography B, 777, pp. 179-189.

Wim Watjen, Gudrun Michels, Barbel Steffan, Petra Niering, Yvonni Chovolou, Andreas Kampkotter, Quynh-Hoa Tran-Thi, Peter Proksch, and Regine Kahl. (2005). Low Concentrations of Flavonoids Are Protective in Rat 1-141TE Cells Whereas High Concentrations Cause DNA Damage and Apoptosis J. Num 135: 525-531.

Kathrin Plochmanna, Gabriele Korte, Eleni Koutsilieri, Elke Richling, Peter Riederer, Axel Rethwilm, Peter Schreier and Carsten Scheller. (2007). Structure-activity relationships of flavonoid-induced cytotoxicity on human leukemia cells. Archives of Biochemistry and Biophysics, Volume 460, Issue 1, Pages 1-9.

Stavreva, M., et al. (2008). Protocol on Toxicological Investigations and Safety Evaluation of DHQ for application in food products, National Center of Public Health and Nutrition, Director Ivanov, L., Ministry of Health, Sofia, Bulgaria. Agreement No. 034-P-2007. Bulgarian language version.

Zhanataev, A. K., Kulakova, A. V., Nasonova, V. V., Dumev, A. D., (2008). In Vivo Study of Dihydroquercetin Genotoxicity. Bulletin of Experimental Biology and Medicine, 145, 3, 309-312. PHARMACOLOGY AND TOXICOLOGY.

Makena, Patrudu S; Pierce, Samuel C; Chung, King-Thom; Sinclair, Scott E; (200.9). Comparative mutagenic effects of structurally similar flavonoids quercetin and taxifolin on, tester strains Salmonella typhimurium TA102 and Escherichia coli WP-2 uvrA. Environmental and molecular mutagenesis (Environ Mol Mutagen), vol. 50 (issue 6):pp. 451-9.

Robinson R R, Feirtag J, Slavin J L, 20(4) J Am Coll Nutr 279-85 (2001).

Ascherio A., Rimm E B, Giovannucci D, Spiegelman M J, Stampfer M J, Willett W C. Dietary fat and risk of coronary heart disease in men: Cohort follow up study in the United States. BMJ 1996; 313, 84-90.

Rimm E B, Ascherio A., Giovannucci D, Spiegelman M J, Stampfer M J, Willett W C. Vegetable, fruit, and cereal fiber intake and risk of coronary disease among men. JAMA 1996; 275, 447-451.

Glore et al., *J. Am. Diet. Assoc.*, 94,425 (1994).
Brown et al., *Am. J. Clin. Nutr.*, 69,30 (1999).
Keenan et al., *Adv. Exp. Med Bioi.*, 427,79 (1997).
Anderson, *Can. J.Cardiol.*, 11, 55G (1995).
Anderson and Hanna, *J. Nutr.*, 129,145S (1999).
Ascherio et al., *Circulation*, 86, 1475 (1992).
Ludwig et al., *JAMA*, 282, 1539 (1999).
Wright et al., *Br. Med. J.*, 2, 1541 (1979).
Schlamowitz et al., Lancet, 2, 622 (1987).
Singh et al., *J. Hum. Hypertens.*, 7,33 (1993).
Saltzman et al., *J. Nutr,* 131,1465 (2001).

FIELD OF THE INVENTION

This invention and disclosure relate to nutritional compounds and methods that reduce and control cardiometabolic risk factors [FIG. 1], associated with metabolic syndrome and hypercholesterolemia in a mammal, specifically, a human.

BACKGROUND OF INVENTION

Overconsumption of a maladaptive, generally, fast food commercialized diet consisting of foods that are calorie-dense, nutritionally-poor, phytochemical-depleted, highly processed and rapidly absorbable has been shown to increase systemic inflammation and reduce insulin sensitivity [1-3]. With chronic ingestion, this dietary pattern often results in metabolic syndrome (MetS) [FIG. 2], a combination of medical disorders that affects a large number of people in a clustered fashion. The metabolic syndrome, also termed "insulin resistance syndrome" is a non-diabetic accumulation of risk factors, which can lead to the development of diabetes but it is not identical with diabetes. As defined by the American Association of Clinical Endocrinology the metabolic syndrome (i.e. the Insulin Resistance Syndrome) is defined by five factors:

1. Elevated waist circumference:
    Men—greater than 40 inches (102 cm)
    Women—greater than 35 inches (88 cm)
2. Elevated triglycerides: Equal to or greater than 150 mg/dL (1.7 mmol/L)
3. Reduced HDL ("good") cholesterol:
    Men—Less than 40 mg/dL (1.03 mmol/L)
    Women—Less than 50 mg/dL (1.29 mmol/L)
4. Elevated blood pressure: Equal to or greater than 130/85 mm Hg or use of medication for hypertension
5. Elevated fasting glucose: Equal to or greater than 100 mg/dL (5.6 mmol/L) or use of medication for hyperglycemia.

The end result of MetS is to increase one's risk for cardiovascular disease and diabetes. In most cases, metabolic syndrome culminates in type 2 diabetes. The symptoms of metabolic syndrome are related to lipid and carbohydrate metabolism and include obesity, elevated triglycerides, low levels of high density lipoproteins, increased blood pressure or hypertension and increased glucose levels, but also symptoms of inflammation [4-7]. As worldwide food consumption patterns shift to the aforementioned dietary pattern, MetS is becoming a significant burden in developing nations and global prevalence is growing [8,9].

It is widely viewed that MetS results from an increasing, perpetual state of whole body insulin resistance, which is strongly associated with dietary carbohydrate [10-12] and saturated fat [13], leading to high serum triglycerides (TG) and visceral adiposity [14-16]. Acute infusion of free fatty acids leads to the accumulation of TG in skeletal muscle and evokes whole body insulin resistance with the same temporal pattern [17-20]. Metabolites of lipid metabolism such as diacylglycerol have been shown to directly induce insulin resistance by chronically activating protein kinase C (PKC). PKC activation terminates insulin signaling, preventing crucial tyrosine phosphorylation by the insulin receptor, leading to impaired insulin signaling [15]. MetS is also associated with a state of chronic inflammation. Adipocyte leakage has recently been shown to result in the recruitment of macrophages, which envelope excess lipids, form foam cells, and release inflammatory cytokines, setting up a state of systemic, chronic inflammation [21,22]. These adipokines lead to the systemic activation of several protein kinases involved in inflammatory signal transduction, including phosphoinositide-3 kinase (P13K), glycogen synthase kinase (GSK-3) and PKC that singly or in concert cause insulin resistance in skeletal muscle and adipose tissue [23-25].

MetS is associated with severe health complications, such as increased risk of atherosclerotic cardiovascular disease [26] and represents a growing public health problem [27]. Development of the MetS is influenced by genetic as well as environmental factors [28, 29]. Cardiovascular diseases (CVD) in patients with MetS culminating by type 2 diabetes are a large and increasing health problem. Increased atherosclerotic lesions are believed to form the basis behind the high frequency of CVD in diabetes. The arterial wall in diabetes harbors not only increased amounts of atherosclerotic plaques, but also diffuse alterations present in non-atherosclerotic parts of the vessel wall. One element of the generalized alterations in the vasculature in diabetes is endothelial dysfunction [33], characterized by increased permeability [34], increased expression of pro-inflammatory molecules [35], and altered vasomotoric responses [36]. Moreover, changes in extracellular matrix components of the tunica media are present in both atherosclerotic and nonatheroscleroticparts of the arterial tree in diabetes. Increased concentrations of collagen type 4 [37], hyaluronic acid [38], osteopontin, osteoprotegerin [39], and metalloproteinases [40] have, for example, been described in conjunction with the presence of high amounts of glucosederived increased cross-linking of collagens [41]. Decreased amounts of several gene products related to apoptosis have been observed in vascular smooth muscle cells from normal appearing areas of arteries from patients with diabetes [42]. In addition, linear media calcifications occur with increased frequency among patients with glucose intolerance and diabetes and are strong predictors of CVD in these individuals [43,44]. In accordance, recent studies of non-atherosclerotic arterial alterations in animal models of type 2 diabetes and hyperglycemia demonstrated increased aortic stiffness and upregulation of matrix components [45], increased arterial calcification [46], and accumulation of glycosaminoglycan-rich material [47]. Thus, defects in several molecular pathways seem to be present in the arterial wall in patients with type 2 diabetes. These changes are likely to play important roles in the arterial response to injury and thus in the build-up of atherosclerotic plaques in diabetic patients. In the recent study it was used transcriptional profiling on well-defined non-atherosclerotic arterial samples from diabetic individuals. Using pathway and network analysis, the data display a statistically significant cluster of dysregulated genes in the arteries of diabetic patients, which is in accordance with the presence of a diffuse diabetic macroangiopathy, similar to the diabetic microangiopathy. This approach has not previously been used, but point towards dysregulated pathways related to matrix metabolism, triglyceride synthesis, inflammation, as well as insulin signaling and apoptosis. Dysregulated gene interactions and pathways in the cells of the arterial wall in diabetes may play important roles in the arterial response to injury and atherosclerosis [48].

In recent years, the contribution of oxidized fats to total energy intake has markedly increased in industrialized countries due to the rising consumption of deep-fried products [49]. In fast food restaurants, foodstuffs are typically fried in fats in fryers at temperatures close to 180° C. During the frying process, several chemical reactions occur within the frying oil resulting in the formation of a mixture of chemically distinct lipid peroxidation products [50]. Large quantities of the frying oil are absorbed into the fried food during deep-frying and therefore ingested during their consumption. Feeding experiments with animals revealed that ingestion of oxidized fats provokes a wide array of biological effects [51-53]. One of the most striking effects of oxidized fat is the induction of oxidative stress which is due to lipid hydroperoxides absorbed from the ingested oxidized fats and reactive oxygen species (ROS) generated from microsomal cytochrome P450 enzymes which are induced by oxidized fat [54-56]. Oxidative stress in animals fed oxidized fats is evident by elevated concentrations of lipid peroxidation products, reduced concentrations of exogenous and endogenous antioxidants, and a decreased ratio of reduced and oxidized glutathione in plasma and tissues [57-60].Recent studies have shown that consumption of oxidized fats leads to a reduction of tocopherol concentrations in animal tissues due to a reduced digestibility and an enhanced turnover of vitamin E [59,60]. Lipid hydroperoxide (LOOH) is a well-known marker of oxidative stress formed from unsaturated phospholipids; glycolipids and cholesterol by peroxidative reactions under oxidative stress. Oxidized low density lipoproteins (OxLDL) is besides membrane-bound cholesterol-derived hydroperoxides, the main form of LOOH responsible for the development of oxidative stress [61]. Lipid peroxides are directly involved in mediating endothelial dysfunction, by increasing the production of thromboxane A, and the expression of cell adhesion molecules in the vasculature, and also in the peripheral vasculature [62].

While studies have shown that increased body mass index (BMI) can pave the way to dementia, studies are now discovering that visceral fat's abnormal metabolic activities make it one of the most important factors where heart risk is concerned. Cholesterol and triglyceride levels generally increase. Average health consequences of excess visceral fat include:

Impacted insulin sensitivity and blood sugar utilization.
Compromised circulation.
Challenged immune system.
Increased inflammatory responses.
Compromised heart health, overall mobility and longevity.

Pre-existing health conditions may be aggravated. There are significant changes in the myocardium during the development of abdominal obesity in the metabolic syndrome [FIG. 3], primarily of ischemic changes in the nature of the imbalance between the sharply increased demands for oxygen and substrates metabolism of hypertrophied cardiomyocytes, and reduced levels of blood supply. Marked interstitial sclerosis and fatty infiltration of the interstitium of myocardium and impede the diffusion of oxygen and substrates of a few capillaries in the working myocardial cells. Increasing energy needs for the cardiomyocytes entails the adaptive hyperplasia of mitochondria. Marked compensatory changes in organelle responsible for calcium metabolism and conjugation of excitation from contraction, hyperplasia, sarcoplasmic reticulum, increases the surface of T-system. However, hypertrophy of cardiomyocytes increases the discrepancy between the mass of muscle fibers and the deficit in the microcirculation, which leads to the breakdown of adaptive mechanisms. Thus, there are destructive and atrophic processes in place. Occurred depression of respiratory function of mitochondria, decreased the binding and capture of $Ca2+$, the accumulation of triglycerides, inhibition of fatty acid oxidation, lipid peroxidation, accumulation of products extended peroxidation in the myocardium. Accumulation of triglycerides and fatty acids in the heart muscle cells leads to disruption of the contractile function of myofibrils, followed by their atrophy and death [63].

Ventricular myocytes contain about 75% of the protein mass of myocardium and provide a significant contribution to the "cardiac hypertrophy". Along with the myocytes in the myocardium, there are other active cells—fibroblasts, smooth muscle cells vascular endothelial cells. All of them are also involved in the development of myocardial pathology, as may produce local factors that can stimulate myocyte hypertrophy. Among these factors can result in endothelin, norepinephrine, angiotensin II, secreted by fibroblasts, tumor necrosis factor, growth factors, etc [63]. Very important question of how mechanical stress is converted into biochemical signals. Suggest that mechanical stress directly alters the conformation of functional proteins or activates enzymes such as phospholipase. Myocyte hypertrophy is an accumulation of proteins (in particular accelerates the synthesis of myofibrillar proteins (e.g., myosin), and ribosomes). The overall rate of protein synthesis is defined as its "effectiveness" (the speed with which the synthesized nascent peptide chains on the ribosome) and its volume (the relative number of ribosomes). The increase in protein mass in cardiac hypertrophy is a result of increasing the volume and efficiency, and synthesis. It is known that myocytes forming arterial and ventricular able to hypertrophic growth. The experiments showed that cardiac myocytes retain the ability to synthesize DNA and re-enter the cell cycle of development. That growth is explained by myocyte hypertrophy, infarction, which is expressed in increasing the mass of the ventricles. Ventricular fibrillation is the form of arrhythmia. The overwhelming majority of sudden cardiac deaths from corollary disease are thought to be from ventricular fibrillation. Atrial Fibrillation (AF), one of the most common kinds of arrhythmias, is responsible for at least 15 to 20 percent of all ischemic strokes [63].

Metabolic syndrome (MetS) is the coexistence of hyperglycaemia, hypertension, dyslipidemia and obesity. Therefore cardiovascular diseases such as coronary heart diseases and stroke are more prevalent among patients with metabolic syndrome [64]. MetS increases the risk of premature death [30, 31, 32], therefore, effective and affordable strategies to assist to reduce cardiometabolic risk factors and control the syndrome would benefit the population at risk. As such, an important aspect to consider in dietary recommendations for MetS is the incorporation of diverse, targeted biologically-active nutritional compounds to address the multiple underlying mechanisms of MetS.

E-148-2010/0 claims hesperidin is a flavonoid compound found in citrus fruits for administration of oral hesperidin to patients with metabolic syndrome to attenuate biomarkers of inflammation and improve blood vessel relaxation, lipid cholesterol profiles, and insulin sensitivity. Thus, claims hesperidin and its active aglycone form, hesperetin, which may be effective agents for the treatment of diabetes, obesity, metabolic syndrome, dyslipidemias, and their cardiovascular complications including hypertension, atherosclerosis, coronary heart disease, and stroke.

US 2011/0306575 A1 provides a method for using processed cellulose for lowering values of risk factor measurements for such diseases as arteriosclerotic cardiovascular disease and diabetes.

EP 1 350 516 B1 claims a hydrophobic licorice extract, and extracts from turmeric, clove and cinnamon for the use of treating metabolic syndrome as well as associated diseases like visceral obesity and diabetes mellitus. The activity of the extracts is measured in reference to troglitazone and pioglitazone.

U.S. Pat. No. 7,202,222 B2 claims dihydroquercetin and root-derived aralosides for the use of treating obesity and fat loss promotion.

CA 2 526 589 A1 describes ligands of PPAR-gamma, in particular glabrene, glabridine, glabrol and their derivatives, and glitazones. These compounds are mentioned in connection with the multiple risk factor syndrome, another name of the metabolic syndrome, which is related to insulin resistance and can be treated with PPAR-gamma ligands. Also described is a licorice extract for the treatment of metabolic syndrome.

JP 2005/097216 mentions dehydrodieugenol A and B, magnolol, oleanic acid and betulic acid as PPAR-gamma ligands that are useful for preventing or ameliorating metabolic syndrome.

U.S. Pat. No. 6,495,173 B1 claims a red yeast rice, coenzyme $Q_{10}$, and chromium with or without inositol hexanicotinate, selenium and mixed tocoferols to reduce or control blood cholesterol, triglycerides, low density lipoproteins, to reduce arterial plaque build-up, atherosclerosis in mammal.

US 2010/0291050 A1 claims a nutritional composition for reducing oxidative damage and lipid peroxidation in humans, where is the compositions comprise adaptogens such as astragalus root, ashwagandha root, cordyceps, holy basil leaf, maca root, reishi mashrooms, schizandra, and suma root; superfruits comprising acerola, camu-camu, pomegranate, bilberry, blueberry, Goji berries, Acai, maitake, citrus bioflavonoids, rose hips and Gingko biloba.

McCue, Patrick et al. (Asia Pacific Journal of Clinical Nutrition 13(4) (2004):401-408) also describe the efficacy of extracts of oregano and specific compounds, e.g. rosmarinic acid and Quercetin on the activity of a-amylase through the inhibition of the enzyme. Symptoms like hyperglycaemia, type 2 diabetes and prediabetes impaired glucose tolerance could be treated.

The essential nutritional novel compounds have been used individually to help in various health pathologies and disorders, and thus have a long history of safe use in humans. However, neither of these compounds has been used to assist in reducing and controlling cardiometabolic risk factors in mammals, and in particular in humans. Thus, there exists a need for nutritional novel compounds to be used as nutraceutical agents for the assistance to prevent and/or manage metabolic syndrome and cardiovascular disorders and related diseases, particularly, cholesterol- or lipid-related disorders, such as, for example, atherosclerosis.

Dihydroquercetin (taxifolin) is the flavonoid compound having molecule structure is based on C6—C3—C6 skeleton consisting of two aromatic rings joined by a three carbon link with the absence of the C2—C3 double bond and have two chiral carbon atoms in position 2 and 3 [FIG. 4]. The A ring of the flavonoid structure being acetate derived (3×C2) and the C and 13 rings originating from cinnamic acid derivatives (phenylpropanoid pathway). Consequently, the B-ring can be either in the (2S)- or (2R)-configuration. The C-3 atom of dihydroflavonol Dihydroquercetin (taxifolin) bears both a hydrogen atom and a hydroxyl group, and is therefore an additional center of asymmetry [73]. Thus, four stereoisomers are possible for each dihydroflavonol structure, (2R, 3R), (2R,3S), (2S,3R), and (2S,3S). All four configurations have been found in naturally occurring dihydroflavonols, but the (2R,3R)-configuration is by far the most common. Conifer wood species, especially those from the family of Pinaceae are considered rich sources of flavonoid Dihydroquercetin (taxifolin) [65-72].

Arabinogalactans are class of long, densely branched low and high-molecular polysaccharides MW: 3,000-120,000 [FIG. 5]. The molecular structures of water-soluble arabinogalactans from different hardwood species have been intensively investigated. Arabinogalactans consist of a main chain of b-D-(1fi3)-galactopyranose units (b-D-(1fi3)-Galp) where most of the main-chain units carry a side chain on C-6 [fi3,6)-Galp-(1fi]. Almost half of these side chains are b-D-(1fi6)-Galp dimers, and about a quarter are single Galp units. The rest contain three or more units. Arabinose is present both in the pyranose (Arap) and furanose (Araf) forms, attached to the side chains as arabinobiosyl groups [b-L-Arap-(1fi3)-LAraf-(1fi] or as terminal a-L-Araf e.g. a single L-arabinofuranose unit or 3-O-(β-L-arabinopyranosyl)-α-L-arabinofuranosyl units [74-77].

After screening of a large number of vegetable by-products, were obtained numerous dietary fibers with exceptional biological antioxidant capacity from fruits and other vegetable materials. These fibers combine in a single material the physiological effects of both dietary fiber and antioxidants [78]. Dietary fiber arabinogalactan from hardwoods, mainly from *Larix dahurica* (*Larix gmelinii*), *Larix sibirica*, *Larix sukaczewii* larch wood species, i.e. larch arabinogalactan can be defined as a fiber containing significant amounts of natural antioxidants, mainly Dihydroquercetin (taxifolin) associated naturally to the fiber matrix with the following specific characteristics: 1. Dietary fiber content, higher than 70% dry matter basis. 2. One gram of dietary fiber larch arabinogalactan should have a capacity to inhibit lipid oxidation equivalent to, at least, 1,000 umol TE/gram basing on ORAC value. 3.

One gram of dietary fiber larch arabinogalactan should have a capacity of Cell-based Antioxidant. Protection (CAP-e) to protect live cells from oxidative damage to, at least 6 CAP-e units per gram, where the CAP-e value is in Gallic Acid Equivalent (GAE) units [FIG. 7]. 4. The antioxidant capacity possess an intrinsic property, derived from natural constituents of the material (soluble in digestive fluids) not by added antioxidants or by previous chemical or enzymatic treatments [FIG. 8]. The table in FIG. 8 shows the results obtained in vitro, and presented in the following order: the antioxidant capacities as determined by the FRAP, TEAC, and deoxyribose assays. All the samples investigated were found to exhibit antioxidative properties. The FRAP assay takes advantage of electron-transfer reactions. Herein, a ferric salt, $Fe(III)(TPTZ)_2Cl_3$ (TPTZ=2,4,6-tripyridyl-s-triazine), is used as an oxidant. The reaction detects species with redox potentials <0.7 V [the redox potential of $Fe(III)(TPTZ)_2$], so FRAP is a reasonable screen for the ability to maintain redox status in cells or tissues. Reducing power appears to be related to the degree of hydroxylation and extent of conjugation in flavonoids. However, FRAP actually measures only the reducing capability based on ferric iron, which is not relevant to antioxidant activity mechanistically and physiologically. The TEAC assay is based on the formation of ferrylmyoglobin radical (from reaction of metmyoglobin with $H_2O_2$), which may then react with ABTS [2,2'-azinobis(3-ethylbenzothiazoline-6)-sulfonic acid] to produce the $ABTS^{*+}$ radical. $ABTS^{*+}$ is intensively colored, and AC is measured as the ability of the test species to decrease the color by reacting directly with the $ABTS^{*+}$ radical. Results of test species are expressed relative to Trolox. Deoxyribose assays: Hydroxyl radicals, generated by reaction of an iron-EDTA complex with $H_2O_2$ in the presence of ascorbic acid, attack deoxyribose to form products that, upon heating with thiobarbituric acid at low pH, yield a pink chromogen. Added hydroxyl radical "scavengers" compete with deoxyribose for the hydroxyl radicals produced and diminish chromogen formation. A rate constant for reaction of the scavenger with hydroxyl radical can be deduced from the inhibition of color formation. For a wide range of compounds, rate constants obtained in this way are similar to those determined by pulse radiolysis. It is suggested that the deoxyribose assay is a simple and cheap alternative to pulse radiolysis for determination of rate constants for reaction of most biological molecules with hydroxyl radicals.

Dihydroquercetin (taxifolin) possess superior antioxidant activity [FIG. 8] to suppress affects of free radicals [79-85]. Dihydroquercetin (taxifolin) can, penetrate the human erythrocytes easily and protect from oxidative damage [FIGS. 6-7]. Protocol for the empirical studies illustrated in FIG. 6 can be described as follows:

For each test product, 0.4 g was mixed with 4 mL 0.9% saline at physiological pH. Products were mixed by inversion and then vortexed. Solids were removed by centrifugation at 2400 rpm for 10 minutes. The supernatant of the products was removed and then filtered for use in the CAP-e assay. Red blood cells were treated in duplicate with serial dilutions of the test products. Negative controls (untreated red blood cells) and positive controls (red blood cells treated with oxidizing agent) were performed in hexaplicate. The antioxidants not able to enter the cells were removed by centrifugation and aspiration of supernatant above the cell pellet. The cells were exposed to oxidative damage by addition of the peroxyl free-radical generator AAPH. Using the indicator dye DCF-DA, which becomes fluorescent as a result of oxidative damage, the degree of antioxidant damage was recorded by measuring the fluorescence intensity of each test sample. The inhibition of oxidative damage was calculated as the reduced fluorescence intensity of product-treated cells, compared to cells treated only with the oxidizing agent. The CAP-e value reflects the IC50 dose of the test product, i.e. the dose that provided 50% inhibition of oxidative damage. This is then compared to the IC50 dose of the known antioxidant Gallic Acid.

Protocol for the empirical studies illustrated in FIG. 7 can be described as follows:

For each test product, 0.3 g was mixed with 3 mL 0.9% saline at physiological pH. Test products were mixed by inversion and then vortexed. After 15 minutes, solids were removed by centrifugation at 2400 rpm for 10 minutes. The supernatant of the product was removed and then filtered for use in the CAP-e assay. Red blood cells were treated in duplicate with serial dilutions of the test products. Samples of untreated red blood cells (negative controls) and samples of red blood cells treated with oxidizing agent but not with an antioxidant-containing test products (positive controls) were prepared in hexaplicate. The antioxidants not able to enter the cells were removed by centrifugation and aspiration of supernatant above the cell pellet. The cells were exposed to oxidative damage by addition of the peroxyl free-radical generator AAPH. Using the indicator dye DCF-DA, which becomes fluorescent as a result of oxidative damage, the degree of antioxidant damage was recorded by measuring the fluorescence intensity of each test sample. The inhibition of oxidative damage was calculated as the reduced fluorescence intensity of product-treated cells, compared to cells treated only with the oxidizing agent. The CAP-e value reflects the IC50 dose of the test product, i.e. the dose that provided 50% inhibition of oxidative damage. This is then compared to the IC50 dose of the known antioxidant Gallic Acid.

Erythrocytes supplemented with Dihydroquercetin (taxifolin) exhibited high resistance against the oxdative stress and haemolysis produced by phenylhydrazine and the lysis induced by osmotic shock. This suggests that Dihydroquercetin (taxifolin) may act by increasing the stability of the erythrocyte membrane. Pre-incubation of RBCs with water-soluble Dihydroquercetin (taxifolin) for 30 min significantly reduced the peroxyl radical (AAPH)-induced hemolysis to 32.5±5.6%. Dihydroquercetin (taxifolin) was highly effective in reducing phospholipase C-induced hemolysis (45.4±10.0% versus vehicle 75.7±5.2%, P<0.001). Dihydroquercetin (taxifolin) showed a greater potency of inhibiting xanthine-oxidase-dependent superoxide generation (EC50: 17.4±3.6 μM vs 70.8±19.3 μM, P<0.001).

Dihydroquercetin (taxifolin) can modulate the expression of several genes, including those coding for detoxification enzymes, cell cycle regulatory proteins, growth factors, and DNA repair proteins. Dihydroquercetin (taxifolin) significantly activates Antioxidant Response Element. ARE (Antioxidant Response Element) in the promoter region of the human NQO1 gene contains AP-1 or AP-1-like DNA binding sites, and AP-1 proteins have been implicated in the formation or function of this and other ARE complexes. Also, ARE-binding proteins in inducing cerebral MT-1 expression and implicates MT-1 as one of the early detoxifying genes in an endogenous defense response to cerebral ischemia and reperfusion [86,87].

It have been demonstrated in numerous studies in vitro and ex vivo that Dihydroquercetin (taxifolin) inhibits lipid peroxidation, a process that often leads to atherosclerosis [88-90]. In an animal study, Dihydroquercetin (taxifolin) inhibited the peroxidation of serum and liver lipids following exposure to toxic ionizing radiation [91]. Dihydroquercetin (taxifolin)'s inhibitory effects on lipid peroxidation are enhanced by both vitamin C and vitamin E [92]. By inhibiting the oxidation of harmful low-density lipoprotein (LDL), Dihydroquercetin (taxifolin) may help prevent atherosclerosis [93].

Dihydroquercetin (taxifolin) can enhance the production of glutathione, block the production of reactive oxygen species, and prevent the late influx of calcium, all of which are activities that prevent specific events in the cell death pathway. Oxidised glutathione concentration and the oxidised/reduced glutathione ratio always increased by proinflammatory stimuli in parenchymal liver cells e.g. cytokines. These effects were significantly prevented by Dihydroquercetin (taxifolin) at all tested concentrations. Glutathione prexidase (GPx) protein level was significantly increased by Dihydroquercetin (taxifolin) in 25 and 50 µM concentrations. Dihydroquercetin (taxifolin) prevented the cell death induced by GSH (glutathione) depletion. For example, taxifolin has an EC50 of 30 µM for the protection of the RGC-5 cells from oxidative stress induced by GSH depletion but an EC50>50 µM for protection of the CNS-derived mouse HT22 cells from a similar insult [94,95].

One of the important ways in which Dihydroquercetin (taxifolin) may limit the cytokines plain is by preventing elevation of oxidized glutathione concentration and the oxidized/reduced glutathione ratio induced by inflammatory cytokines [96]. Dihydroquercetin (taxifolin) prevents calcium influx, the last step in the cell death process. By inducing the expression of antioxidant defense enzymes, it has the potential to have long-lasting effects on cellular function. This, in turn, could be highly beneficial to cells exposed to chronic oxidative stress [97]. Dihydroquercetin (taxifolin) processes benefit results in both intracellular and extracellular environments. Studies in erythrocytes, mast cells, leucocytes, macrophages and hepatocytes have shown that Dihydroquercetin (taxifolin) renders cell membranes more resistant to lesions. Dihydroquercetin (taxifolin) protects the inner walls of the blood vessels and capillaries against destructive enzymes, decay and free radical damage [98].

Partial degradation of Dihydroquercetin (taxifolin) by GIT microbiota results in the formation of 3,4-dihydroxyphenilacetic acid, another valuable antioxidant. Effect of the this microbial phenolic 3,4-dihydroxyphenylacetic acid (3,4-DHPAA), on modulation of the production of the main pro-inflammatory cytokines (TNF-α, IL-1β and IL-6) had been yet confirmed. The production of these cytokines by lipopolysaccharide (LPS)-stimulated peripheral blood mononuclear cells (PBMC) pre-treated with the phenolic metabolite was studied in healthy volunteers. With the exception of 4-HHA for TNF-α secretion, the dihydroxylated compound, 3,4-DHPAA significantly inhibited the secretion of these pro-inflammatory cytokines in LPS-stimulated PBMC. Mean inhibition of the secretion of TNF-α by 3,4-DHPAA was 86.4%. The concentrations of IL-6 in the culture supernatant were reduced by 92.3% with 3,4-DHPAA pre-treatment. Finally, inhibition was slightly higher for IL-1β on 97.9% by 3,4-DHPAA. These results indicate that dihydroxylated phenolic acids derived from microbial metabolism of Dihydroquercetin (taxifolin) present marked anti-inflammatory properties, providing additional information about the health benefits of dietary polyphenols and their potential value as therapeutic agents [99]. It has been shown that microbial metabolites such as 3,4-dihydroxyphenylacetic were more effective than rutin and quercetin precursors in inhibiting platelet aggregation in vitro [100].

Dihydroquercetin (taxifolin) may have applications to assist in the management of stroke, a crippling, often fatal condition marked by a diminished supply of blood and oxygen to the brain. Studies of the effects of oxygen deprivation in rat brains demonstrated that Dihydroquercetin (taxifolin) helps to decrease the damage caused by lack of blood flow [101]. Additionally, Dihydroquercetin (taxifolin) helps to restore normal structure and electrochemical activity to nerve synapses, the junctions that allow nerve cells to transmit information [102].

Infarction in adult rat brain was induced by middle cerebral arterial occlusion (MCAO) followed by reperfusion to examine whether Dihydroquercetin (taxifolin) could reduce cerebral ischemic reperfusion (CI/R) injury. Dihydroquercetin (taxifolin) administration (0.1 and 1.0 microg/kg, i.v.) 60 min after MCAO ameliorated infarction (by 42%+/−7% and 62%+/−6%, respectively), which was accompanied by a dramatic reduction in malondialdehyde and nitrotyrosine adduct formation, two markers for oxidative tissue damage. Overproduction of reactive oxygen species (ROS) and nitric oxide (NO) via oxidative enzymes (e.g., COX-2 and iNOS) was responsible for this oxidative damage. Dihydroquercetin (taxifolin) inhibited leukocyte infiltration, and COX-2 and iNOS expressions in CI/R-injured brain. Dihydroquercetin (taxifolin) also prevented Mac-1 and ICAM-1 expression, two key counter-receptors involved in firm adhesion/transmigration of leukocytes to the endothelium, which partially accounted for the limited leukocyte infiltration. ROS, generated by leukocytes and microglial cells, activated nuclear factor-kappa B (NF-kappaB) that in turn signaled up-regulation of inflammatory proteins. NF-kappaB activity in CI/R was enhanced 2.5-fold over that of sham group and was inhibited by Dihydroquercetin (taxifolin). Production of both ROS and NO by leukocytes and microglial cells was significantly antagonized by Dihydroquercetin (taxifolin). These data suggest that amelioration of CI/R injury by Dihydroquercetin (taxifolin) may be attributed to its anti-oxidative effect, which in turn modulates NF-kappaB activation that mediates CI/R injury [103].

Dihydroquercetin (taxifolin) is known to inhibit HMG-CoA reductase, a key enzyme in cholesterol synthesis [104] and lower plasma triglycerides levels [105, 106]. It is consistent with the activity of other compounds used for the mitigating neglect effects of hypercholesteremia (e.g. statins), which reduce cholesterol and/or triglycerides levels [105]. The effects of Dihydroquercetin (taxifolin) on lipid, apolipoprotein B (apoB), and apolipoprotein A-I (apoA-I) synthesis and secretion were determined in HepG2 cells. Pretreatment of cells with (+−)-taxifolin led to an inhibition of cholesterol synthesis in a dose-and time-dependent manner, with an 86+−3% inhibition at 200 umol observed within 24 h. As to the mechanism underlying this inhibitory effect, Dihydroquercetin (taxifolin) was shown to inhibit the activity of HMG-CoA reductase by 47+−7%. In addition, cellular cholesterol esterification, and triacylglycerol and phospholipid syntheses, were also significantly suppressed in the presence of Dihydroquercetin (taxifolin). ApoA-I and apoB synthesis and secretion were then studied by pulse-chase experiments. ApoA-I secretion was found to increase by 36+−10%. In contrast, an average reduction of 61+−8% in labeled apoB in the medium was apparent with Dihydroquercetin (taxifolin) [107]. Dihydroquercetin (taxifolin) was shown to markedly reduce apoB secretion under basal and lipid-rich conditions up to 63% at 200 micromol/L. As to the mechanism underlying this effect, was examined whether Dihydroquercetin (taxifolin) exerted its effect by limiting triglycerides (TG) availability in the microsomal lumen essential for lipoprotein assembly. Dihydroquercetin (taxifolin) was shown to inhibit microsomal TG synthesis by 37% and its subsequent transfer into the lumen (−26%). The reduction in synthesis was due to a decrease in diacylglycerol acyltransferase (DGAT) activity (−35%). The effect on DGAT activity was found to be non-competitive and non-transcriptional in nature. Both DGAT-1 and DGAT-2 mRNA expression remained essentially unchanged suggesting the point of regulation may be at the post-transcriptional level. Evidence is accumulating that microsomal triglyceride transfer protein (MTP) is also involved in determining the amount of lumenal TG available for lipoprotein assembly and secretion. Dihydroquercetin (taxifolin) was shown to inhibit this enzyme by 41%. Whether the reduction in TG accumulation in the microsomal lumen is predominantly due to DGAT and/or MTP activity remains to be addressed. In summary, Dihydroquercetin (taxifolin) reduced apoB secretion by limiting TG availability via DGAT and MTP activity [108].

The in vivo studies demonstrated improved glucose tolerance, lower insulin levels, lower triglyceride (TG) mass in tissues, lower plasma TG and cholesterol levels, and a decrease in serum ApoB levels as the results of Dihydroquercetin (taxifolin) exposure. These metabolic benefits are due at least in part to peroxisome proliferator-activated receptor (PPAR) activation that occurred like in case of Dihydroquercetin (taxifolin) supplementation. Dihydroquercetin (taxifolin) and its metabolites may exert their effect on PPAR expression indirectly by affectin protein signaling upstream of PPARa and PPARy or by direct binding activity, as well as with observed effects on protein downstreat of PPAR such as ApoA and GLUT2. Dihydroquercetin (taxifolin) supplementation of HepG2 cells resulted in an increase of PPARa expression. Results for PPARy were nearly identical to those for PPARa. The activation dosage was established up to 100 μM in mice. Dihydroquercetin (taxifolin) is associated with dose dependent increase in both PPARa and PPARy expressions [109]. DI-IQ results in the phosphorylation of the insulin receptor and IRS-1, thus enhancing insulin signaling within the cell [110,111]. Since PPARa and PPARy can be activated by phosphorylation through the insulin sensitive P13 kinase pathway, the possibility exists that PPARa and PPARy upregulation occurred as the result of insulin mimic action by Dihydroquercetin (taxifolin). PPAR activation could be occurring through epidermal growth factor inhibition (EGF). EGF and PDGF (platelet derived growth factor) both, when activated, inhibit PPARy expression through MAP kinase signaling, which in turn inhibited by Dihydroquercetin (taxifolin). The Dihydroquercetin (taxifolin) mediated PPAR response can in turn improve glucose uptake into cells, enhance insulin sensitivity, improve lipid metabolism and lipid biomarkers, reduce weight gain, and even beneficially impact endothelial function, inflammation, and other CVD risk factors. Microsomal lipid peroxidation induced by NADPH-cytochrome P-450 reductase was also inhibited by Dihydroquercetin (taxifolin). Dihydroquercetin (taxifolin) protected peroxy radical-damaged mitochondria with no effect on enzyme activity [112] In this way, Dihydroquercetin (taxifolin) has the potential to effectively support in fighting with insulin resistance, diabetes, and heart disease, which is so prelevant around the world. Dihydroquercetin (taxifolin) also stabilize blood vessels and protect against factors that cause atherosclerosis and cardiac, hepatic, and bronchio-pulmonary diseases.

It had been studied the effects of Dihydroquercetin (taxifolin) on functional activity of polymorphonuclear neutrophils from patients with non-insulin-dependent diabetes mellitus. Dihydroquercetin (taxifolin) dose-dependently suppressed generation of anion radicals and hypochlorous acid and production of malonic dialdehyde during oxidation of neutrophil membranes. Dihydroquercetin (taxifolin) decreased activities of protein kinase C and myeloperoxidase in activated polymorphonuclear neutrophils and could bind transition metals ($Fe^{2+}$). These properties determine the ability of Dihydroquercetin (taxifolin) to decrease in vivo functional activity of polymorphonuclear neutrophils from patients with non-insulin-dependent diabetes mellitus [113]. Dihydroquercetin (taxifolin) has been found to help in protection against two common causes of vision loss: macular degeneration and cataract in diabetics. Macular degeneration occurs when an area of the eye's retina that is responsible for detailed vision begins to deteriorate. Dihydroquercetin (taxifolin) promotes blood flow to this region of the eye, which offers protection against vision loss. Also; by inhibiting the activity of an enzyme in the eye lens, Dihydroquercetin (taxifolin) may help to prevent cataract formation in diabetic patients [114,115].

Dihydroquercetin (taxifolin) prevented the increase in serum aspartate and alanine aminotransferase activities due to the inflammatory reaction and stimulated liver ATP phosphohydrolase activity [116]. Dihydroquercetin (taxifolin) had been evaluated by different studies as the small-molecule regulator of signalling cascades as promising anti-inflammatory agent with biological targets such as COX-2, and related pro-inflammatory mediators (cytokines and chemokines, interleukins [ILs], tumour necrosis factor [TNF]-α, migration inhibition factor [MIF], interferon [IFN]-γ and matrix metalloproteinases [MMPs]) implicated in uncontrolled, destructive inflammatory reaction. Dihydroquercetin (taxifolin) was effective with relevant biological targets that include nuclear transcription factor (NF-κB), p38 mitogen-activated protein kinases (MAPK) and Janus protein tyrosine kinases and signal transducers and activators of transcription (JAK/STAT) signalling pathways has received growing attention [117-119]. Dihydroquercetin (taxifolin) had a significant inhibitory effect on the production of cytokines, formation of ROS and NO and change in intracellular Ca2+ levels in dendritic cells of bone marrow and spleen [120]. Dihydroquercetin (taxifolin) was attributed to its inhibitory effects on tyrosinase enzymatic activity, despite its effects on increasing tyrosinase protein levels [121].

Studies indicate that dihydroquercetin is highly safe and efficacious. In fact, research suggests that dihydroquercetin is even safer than its nutritional cousin, quercetin [122,123]. No toxic effects were observed in rats that were treated with high levels of dihydroquercetin for long periods of time [124-131].

Digestive disorders are very common and affect a great number of the population. The typical American diet, which is low in fiber and high in protein and carbohydrate, is a factor in the prevalence of these digestive disorders. Low levels of short-chain fatty acids and elevated levels of ammonia are associated with this type of diet. Intake of fiber, particularly Larch Arabinogalactan, has been shown to be supportive in combating the detrimental effects caused by poor diet. Larch Arabinogalactan has been shown to increase short-chain fatty acids, decrease colonic ammonia levels, increase the numbers of beneficial bacteria in the colon, as well as improve the immune response. These favorable effects of Larch Arabinogalactan have a positive modulation of many of these too-common intestinal factors [132].

Intestinal tracts are exposed to many substances—from antibiotics to protozoal parasites to sugary, processed foods—that create an unfavorable atmosphere in the colon. The result can be constipation, diarrhea, candidiasis, parasitical infections and other conditions attributable to poor colon health. Colon cleansing is an important way to minimize the digestive tract's exposure to the multitude of micro-organisms encountered daily. Yet, relatively speaking, a properly functioning colon is actually quite clean compared to one that is filled with toxic substances, parasites, and pathogenic yeasts, fungi, and bacteria.

Larch Arabinogalactan is also believed to act as a prebiotic; it stimulates the colonic growth of such bacteria as bifid bacteria and lactobacilli that confer certain health benefits. Ingestion of Larch Arabinogalactan has a significant effect on enhancing beneficial gut microflora, specifically increasing anaerobes such as *Lactobacillus*.

Short chain fatty acids, primarily acetate, propionate, and butyrate, are produced in the colon by fermentation of dietary carbohydrates, particularly from degradation-resistant starches and dietary fiber, play an important role in intestinal health. These acids are the principal energy source for the colonic epithelial cells. The non-absorbed fiber of Arabinogalactan is easily fermented by the distal gut microflora, resulting in an elevated production of short-chain fatty acids, primarily butyrate, and, to a lesser extent, propionate.

Ammonia is produced as a by-product in the colon by bacterial fermentation of protein and other nitrogen-containing substances. Research indicates that ammonia levels as low as 5 mmol/L can have detrimental effects on epithelial cells that line the colon. The toxicity of ammonia toward colonic epithelial cells can lead to cell destruction and increased turnover of these cells.

Many clinicians use prebiotics as a supplemental support for intestinal conditions including diverticulosis, leaky-gut, irritable bowel syndrome, as well as inflammatory bowel diseases such as Crohn's disease and ulcerative colitis. Studies have shown that Larch Arabinogalactan consumption reduces intestinal ammonia generation [132]. Since even low ammonia levels can have damaging effects on intestinal colonic cells, Larch Arabinogalactan can be supportive to patients who are unable to detoxify ammonia.

The relationship between dietary fiber intake and cardiometabolic risk factors has been noted in many studies [133, 134]. The use of soluble fibers is one of the diet strategies shown to decrease serum cholesterol concentrations [135]. Based on data from controlled clinical trials it has been estimated that daily intake of 2-10 grams, per day (g/d) of soluble fiber significantly decreases total and LDL-cholesterol [136].

Besides a hypolipidemic effect, there is a growing body of literature suggesting that soluble fibers also lower blood pressure [137] and cardiovascular disease (CVD) risk in general [138,139]. Soluble, dietary fiber consumption has been inversely related to hypertension [140] and diastolic blood pressure [141.] and several intervention studies of soluble fibers have reported blood pressure reductions in both hypertensive and normotensive individuals [142-145]. However, the practical utility of soluble fibers as hypocholesterolemic and hypotensive agents is often limited by the lower gastrointestinal side effects associated with increased consumption and related to their fermentability. Many trials have investigated the effects of soluble, dietary fiber on cardiometabolic risk factors. For example, several trials have been conducted to test the effectiveness of various soluble, dietary fibers to modify cardiovascular disease. Results, however, have been highly variable. Furthermore, despite multiple theories of the mechanism by which soluble fiber acts to decrease serum cholesterol levels and attenuate glucose and insulin response, it is still unclear how such fibers exert their effects.

Dietary fiber arabinogalactan from hardwoods, mainly from larch wood species, i.e. larch arabinogalactan can be defined as a fiber containing significant amounts of natural antioxidants, mainly Dihydroquercetin (taxifolin) [FIGS. 7-8] associated naturally to the fiber matrix with the following specific characteristics: 1. Dietary fiber content, higher than 70% dry matter basis. 2. One gram of dietary fiber larch arabinogalactan should have a capacity to inhibit lipid oxidation equivalent to, at least, 1,000 umol TE/gram basing on ORAC value. 3. One gram of dietary fiber larch arabinogalactan should have a capacity of Cell-based Antioxidant Protection (CAP-e) to protect live cells from oxidative damage to, at least 6 CAP-e units per gram, where the CAP-e value is in Gallic Acid Equivalent (GAE) units. 4. The antioxidant capacity possess an intrinsic property, derived from natural constituents of the material (soluble in digestive fluids) not by added antioxidants or by previous chemical or enzymatic treatments.

Except soluble dietary fiber larch arabinogalactan, the practical use of soluble fibers is limited by the untoward side effects associated with increased consumption. Studies have reported gastrointestinal discomfort, including flatulence, bloating, nausea, feeling of fullness, and loose stools. In addition, many soluble fibers have marginal palatability (e.g., guar gum) or are difficult to consume frequently because of their energy content (e.g., oatmeal). These issues limit the quantity of soluble fiber a person can consume, and thus, limit the amount of benefit to be experienced. However, soluble dietary fiber larch arabinogalactan and larch arabinogalactan consisting naturally with flavonoid Dihydroquercetin (taxifolin) possess minimum discomfort for consumers with mentioned side effects, same time delivers effectiveness to attenuate cardiometabolic risk factors. It has been now discovered that nutritional compounds Dihydroquercetin (taxifolin), Arabinogalactan, and Arabinogalactan combined with Dihydroquercetin (taxifolin) are effective to reduce and control cardiometabolic risk factors associated with metabolic syndrome and hypercholesterolemia in a mammal, specifically a human, resulting in the enhancement of metabolism, reducing or control levels of cholesterol and triglycerides, reducing oxidative damage in humans and resultant health benefits.

SUMMARY OF THE INVENTION

It is the goal of the present invention to provide nutritional compounds Dihydroquercetin (taxifolin), Arabinogalactan, and Arabinogalactan combined with Dihydroquercetin (taxifolin) and a nutritional composition or preparation comprises one or more of these active nutritional compounds with particular exceptional potential to reduce and control cardiometabolic risk factors associated with metabolic syndrome and hypercholesterolemia in a mammal, specifically a human, resulting in the enhancement of metabolism, reducing or control levels of cholesterol and triglycerides, reducing oxidative damage in humans and resultant health benefits.

Therefore the present invention provides the use of a plant extracts in the form of nutritional compounds Dihydroquercetin (taxifolin), Arabinogalactan, and Arabinogalactan combined with Dihydroquercetin (taxifolin) for the production of a nutritional composition or preparation to reduce and control cardiometabolic risk factors, wherein the plant extracts in the form of nutritional compounds are from coniferous wood selected, from the group consisting of wood of *Larix* genus;
spruce wood of the genus *Picea*;
fir wood of the genus *Abies*;
pine wood of the genus *Pinus*;
wood of *Pseudotsuga* genus
or the wood is hardwood.

Thus, the nutritional composition or preparation according to the present invention and nutritional compounds Dihydroquercetin (taxifolin), Arabinogalactan, and Arabinogalactan combined with Dihydroquercetin (taxifolin) itself keeps you healthy, brings the anti-cardiometabolic risk factors solution, prevents and/or control and/or reduce the metabolic syndrome disorders and/or makes you happy in your physiological state.

One object of the present invention is the use of a nutritional composition or preparation comprising Dihydroquercetin (taxifolin), Arabinogalactan, and Arabinogalactan combined with Dihydroquercetin (taxifolin) as anti-cardiometabolic risk agents, wherein the composition or preparation is administered orally to mammals, specifically humans. Preferably Dihydroquercetin (taxifolin), Arabinogalactan, and Arabinogalactan combined with Dihydroquercetin (taxifolin) separately or in combination are the only active anti-cardiometabolik risk ingredients in the composition or preparation.

In further embodiments of the present invention also derivatives such as esters and physiologically/nutraceutically/pharmaceutically acceptable salts of Dihydroquercetin (taxifolin), Arabinogalactan, and Arabinogalactan combined with Dihydroquercetin (taxifolin) may be used instead of nutritional compounds Dihydroquercetin (taxifolin), Arabinogalactan, and Arabinogalactan combined with Dihydroquercetin (taxifolin). It is also possible to use a mixture of nutritional compounds and their derivatives.

In further embodiments the metabolic syndrome is associated with diabetes, obesity, dyslipidaemia, hypolipidaemia, insulin resistance or arteriosclerosis. Cardiovascular diseases are a consequence of metabolic syndrome and can also be an associated indicator of metabolic syndrome. Symptoms of these diseases normally occur in the development of metabolic syndrome and can be attenuated by the inventive preparations.

In some embodiments, the present invention is directed to reducing triglyceride levels, reducing total cholesterol, reducing mean VLDL-cholesterol, and decreasing lipoproteins in humans having cardiometabolic risk factors associated with metabolic syndrome and hypercholesterolemia.

The methods of the invention preferably result in achieving at least three of the following (preferably four, most preferably all five): lowering triglyceride levels, raising HDL-cholesterol levels, lowering LDL-cholesterol levels, lowering Apo C levels, and/or lowering fibrinogen levels in the human during nutritional intake period of nutritional compounds separately or in combination.

Another further object of the invention is the use of nutritional compounds to suppress affects of free radicals on a living cells and protect from oxidative damage, to help in inhibiting lipid peroxidation, a process that often leads to atherosclerosis, microsomal lipid peroxidation induced by enzymes, to help to render cell membranes more resistant to lesions, to protects the inner walls of the blood vessels and capillaries against destructive enzymes, decay and free radical damage.

Another further object of the invention is the use of nutritional compounds to modulate the expression of several genes, including those coding for detoxification enzymes, cell cycle regulatory proteins, growth factors, and DNA repair proteins, to activate Antioxidant Response Element, early detoxifying genes in an endogenous defense response to cerebral ischemia and reperfusion, help to enhance the production of glutathione, help to block the production of reactive oxygen species, and to assist in preventing the late influx of calcium, all of which are activities that prevent specific events in the cell death pathway.

Another further object of the invention is the use of nutritional compounds to modulate of the production of the main pro-inflammatory cytokines as promising anti-inflammatory agents with biological targets such as COX-2, and related pro-inflammatory mediators (cytokines and chemokines, interleukins [ILs], tumour necrosis factor [TNF]-$\alpha$, migration inhibition factor [MIF], interferon [IFN]-$\gamma$ and matrix metalloproteinases [MMPs]) implicated in uncontrolled, destructive inflammatory reaction.

Further the invention relates to the use of nutritional compounds to supportive in combating the detrimental effects caused by poor diet, wherein the nutritional compounds has been shown to increase short-chain fatty acids, decrease colonic ammonia levels, increase the numbers of beneficial bacteria in the colon, as well as improve the immune response.

In particular, the invention relates to the use of nutritional compounds as mentioned above to effectively support in fighting with insulin resistance, diabetes, and heart disease, stabilize blood vessels and protect against factors that cause atherosclerosis and cardiac, hepatic, and bronchio-pulmonary diseases e.g. for maintaining and/or improving mammals cardiometabolic physiological state and health, prevention of cardiometabolic risk factors e.g. increasing healthy lifestyle level in mammals, providing support to maintain healthy lifestyle level in mammals, specifically a human, and lessening cardiometabolic and/or metabolic syndrome problems.

Other features of the present invention will become apparent. Additional advantages and novel features of the invention will also become more apparent to those skilled in the art upon examination of the following or upon learning by practice of the invention.

BRIEF DESCRIPTION OF DRAWINGS AND ILLUSTRATIVE EMBODIMENTS

The following drawings form part of the present specification and are included to further demonstrate certain aspects of the present invention. The invention may be better understood by reference to one or more of these drawings in combination with the detailed description of specific embodiments presented herein.

FIG. 8 depicts the antioxidant capacities results in vitro obtained for Dihydroquercetin (taxifolin) and Larch Arabinogalactan in combination with Dihydroquercetin (taxifolin), where the antioxidant capacities are determined by the FRAP, TEAC, and deoxyribose assays.

DETAILED DESCRIPTION OF THE INVENTION

This invention utilizes nutritional compounds Dihydroquercetin (taxifolin), Arabinogalactan, and Arabinogalactan combined with Dihydroquercetin (taxifolin) in nutritional composition or preparation whether by enhancing the diet with specific low glycemic dietary soluble fiber Arabinogalactan and phytochemical supplementation by Dihydroquercetin (taxifolin) could improve cardiometabolic outcomes in subjects associated with metabolic syndrome (MetS) and hypercholesterolemia, wherein low glycemic load diet with a combination of phytochemicals addressing multiple inflammatory and insulin signaling pathways simultaneously are a novel, effective means to managing MetS. This comprehensive, supplemented lifestyle program represents a potentially powerful approach to the management of at risk individuals with MetS and hypercholesterolemia.

Figure 1:
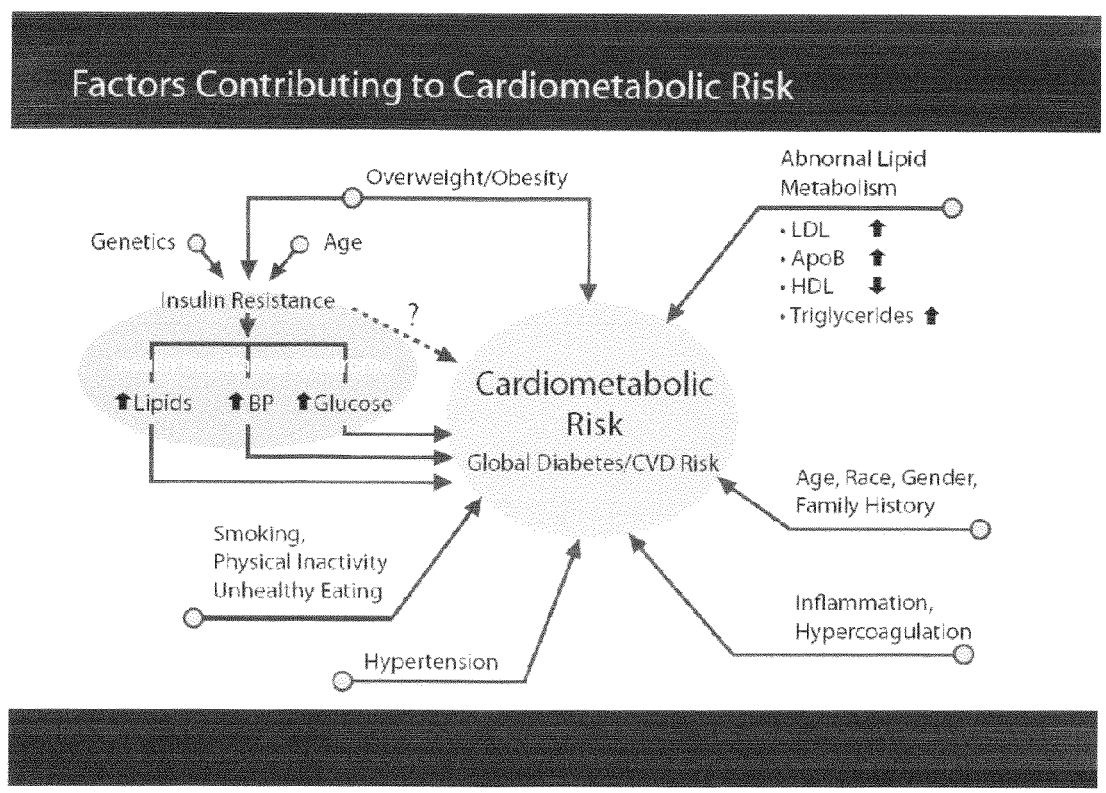
FIG. 1 depicts different cardiometabolic risk factors.
Figure 2:
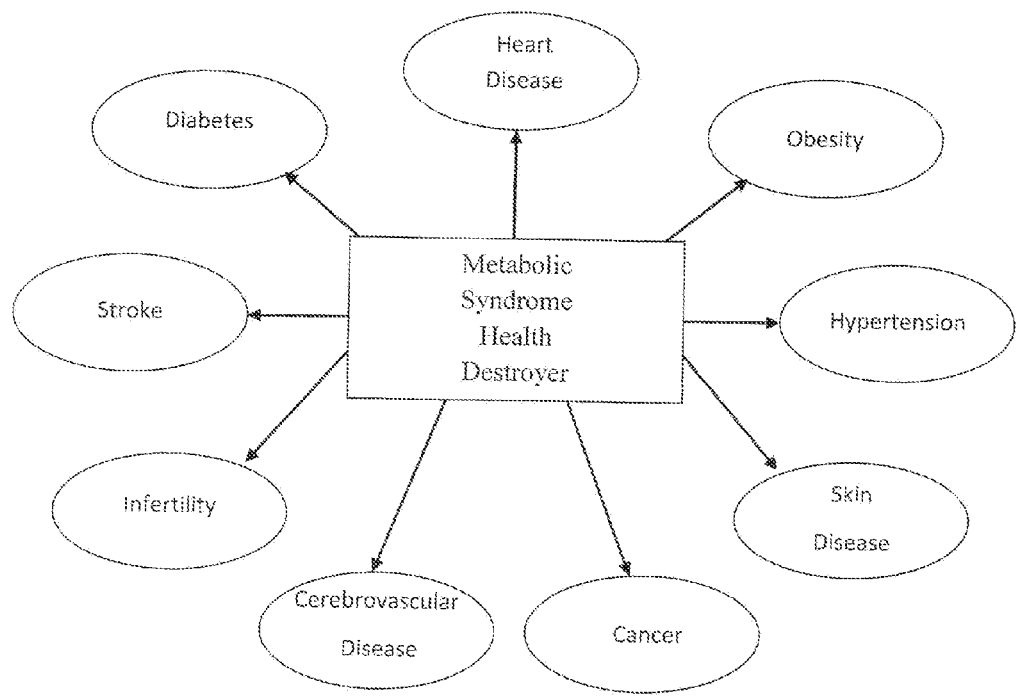
FIG. 2 depicts the Metabolic Syndrome (MetS) disorders, the combination of medical disorders that affect a large number of people in a clustered fashion.
Figure 3:
FIG. 3 depicts the accumulation of fatty tissue and how it envelopes the heart.
Figure 4:
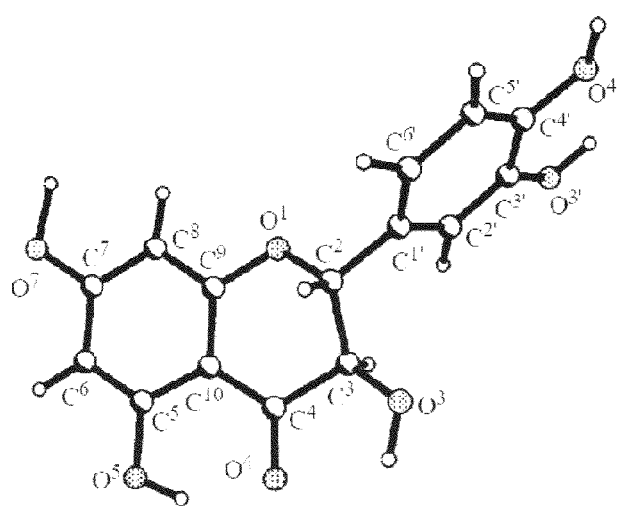
FIG. 4 depicts steric structure of Dihydroquercetine (taxifolin) molecule.
Figure 5:
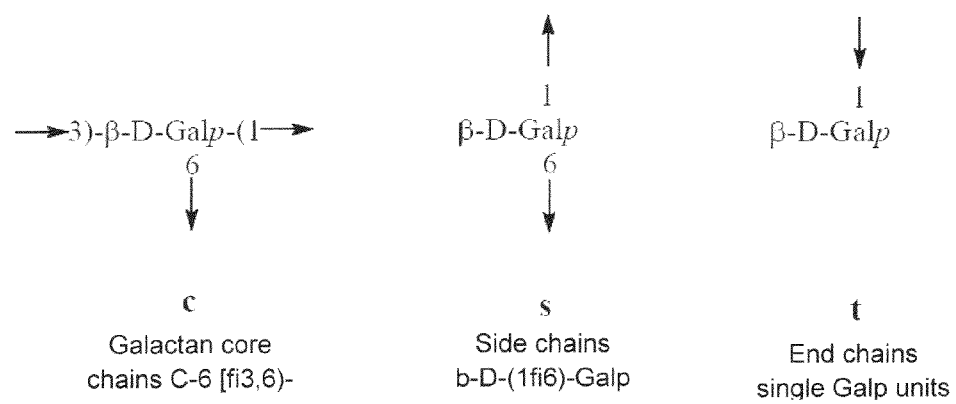
FIG. 5 depicts Larch Arabinogalactan molecule component units.
Figure 6:
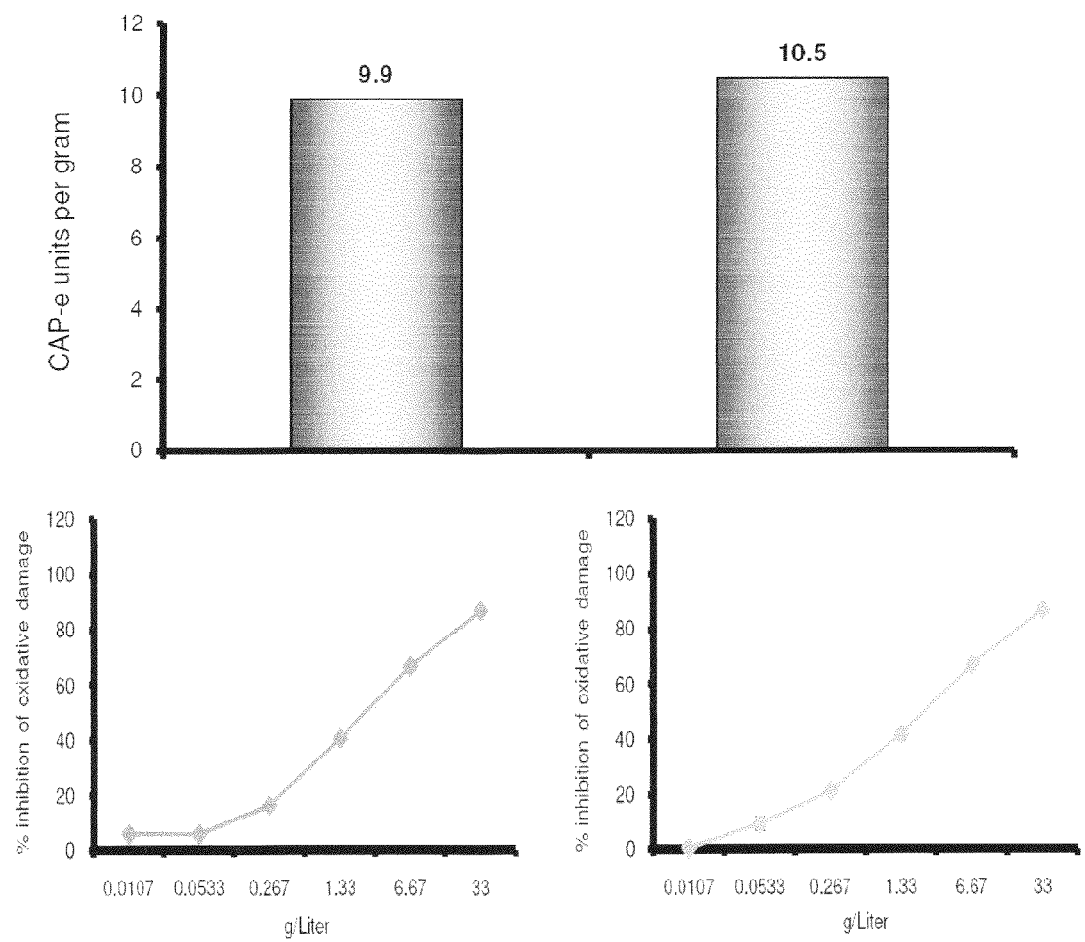
FIG. 6 depicts mean of antioxidant capacity ex vivo of Dihydroquercetin (taxifolin)—Cell-based Antioxidant Protection (CAP-e) against peroxyl radical.
Figure 7:
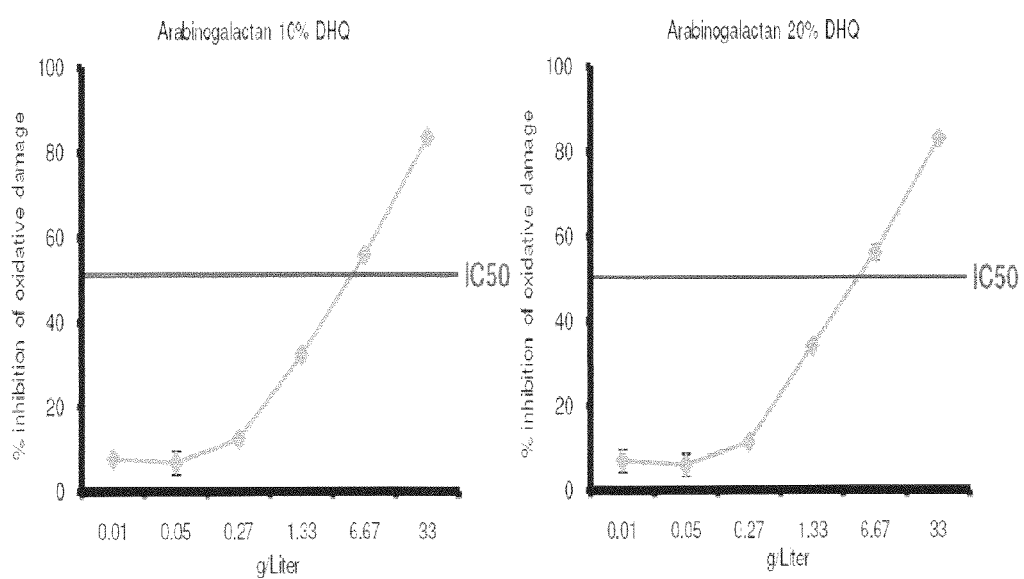
FIG. 7 depicts mean of antioxidant capacity of Larch Arabinogalactan in combination with Dihydroquercetin (taxifolin)—Cell-based Antioxidant Protection (CAP-e) against peroxyl radical.

Also disclosed herein is the method of reducing or control cardiometabolic risk factors associated with metabolic syndrome and hypercholesterolemia or preventing metabolic syndrome and hypercholesterolemia with a preparation described herein. "Preventing" or "prevention" herein does not require absolute success in the sense of an absolute prevention but indicates a reduced risk of developing metabolic syndrome and hypercholesterolemia. FIG. 1 depicts different cardiometabolic risk factors, wherein most therapeutic treatments for hypercholesterolemia focus on achieving LDL goals recommended by NCEP. However, the NHANES 2003-2004 showed that despite better control of LDL, other lipid risk factors remained suboptimal in many US adults, particularly among those with CVD, diabetes, or MetS. Non-HDL cholesterol, a stronger predictor of CVD and mortality risk than LDL, has now been added by the NCEP Adult Treatment Panel III as a secondary target of therapy. In addition, because apo B indicates the total number of atherogenic lipoprotein particles and apo A-I, a major lipoprotein in HDL, has a critical role in reverse cholesterol transport, the apo B/apo A-I (as well as apo B concentration) has been proposed as a risk factor for CVD. Increasing evidence from multiple studies has repeatedly shown that the apo B/apo A-I predicts cardiovascular risk—the lower the ratio, the lower is the risk—and is a better marker than LDL and lipid ratios. In the Inter-Heart study, the, apo B/apo A-I was the strongest determinant of MI risk, even higher than smoking. It can be stated the apo B/apo A-I might be the best marker of the balance of atherogenic and antiatherogenic particles.

The term Dihydroquercetin (taxifolin) as used herein refers to flavonoid Dihydroquercetin (taxifolin) obtainable from natural sources such as from products and by-products derived from coniferous wood or the wood is hardwood by extraction and/or purification. The purity of flavonoid Dihydroquercetin (taxifolin) can be determined by methods known to a person skilled in the art such as e.g. by HPLC, or LC-MS. Furthermore, the term Dihydroquercetin (taxifolin) also encompasses physiologically//nutraceutically/pharmaceutically acceptable salts and esters. One or several of the hydoxy groups of Dihydroquercetin (taxifolin) may also be etherified or esterified to form for example acetates.

Examples of references that deal with the extraction of Dihydroquercetin (taxifolin) from coniferous wood or the wood is hardwood by extraction and/or purification are WO Pat. No. 00/37479; WO Pat. No. 2010/095969 A1; U.S. Pat. No. 5,756,098; EP Pat. No. 86608; U.S. Pat. No. 5,116,969 which disclose a methods of extraction and/or purification of Dihydroquercetin (taxifolin).

The term Arabinogalactan as used herein refers to polysaccharide Arabinogalactan obtainable from natural sources such as from products and by-products derived from coniferous wood or the wood is hardwood by extraction and/or purification. The purity of polysaccharide Arabinogalactan can be determined by methods known to a person skilled in the art such as e.g. by HPLC, or LC-MS or Analysator or size exclusion chromatography (SEC). Furthermore, the term Arabinogalactan also encompasses physiologically//nutraceutically/pharmaceutically acceptable salts and esters.

Examples of references that deal with the extraction of polysaccharide Arabinogalactan from coniferous wood or the wood is hardwood are U.S. Pat. No. 5,756,098; EP Pat. No. 86608; U.S. Pat. Nos. 4,950,751; 1,339,489; 1,861,933; 2,832,765; 3,337,526; 1,358,129; 2,073,616; 3,325,473; 5,116,969; 1,913,607; 2,008,892 which disclose a methods of extraction and/or purification of polysaccharide Arabinogalactan.

The term Arabinogalactan combined with Dihydroquercetin (taxifolin) as used herein refers to substance of polysaccharide Arabinogalactan combined with flavonoid Dihydroquercetin (taxifolin) and obtainable from natural sources such as from products and by-products derived from coniferous wood or the wood is hardwood by extraction and/or purification i.e. arabinogalactan can be defined as a fiber containing significant amounts of natural antioxidants, mainly Dihydroquercetin (taxifolin) associated naturally to the polysaccharide or fiber matrix with the following specific characteristics: 1. Dietary fiber content, higher than 70% dry matter basis. 2. One gram of dietary fiber larch arabinogalactan should have a capacity to inhibit lipid oxidation equivalent to, at least, 1,000 umol TE/gram basing on ORAC value. 3. One gram of dietary fiber larch arabinogalactan should have a capacity of Cell-based Antioxidant Protection (CAP-e) to protect live cells from oxidative damage to, at least 6 CAP-e units per gram, where the CAP-e value is in Gallic Acid Equivalent (GAE) units. 4. The antioxidant capacity possess an intrinsic property, derived from natural constituents of the material (soluble in digestive fluids) not by added antioxidants or by previous chemical or enzymatic treatments. The purity of Arabinogalactan combined with Dihydroquercetin (taxifolin) can be determined by methods known to a person skilled in the art such as e.g. by HPLC, or LC-MS or Analysator or size exclusion chromatography (SEC). Furthermore, the term Arabinogalactan combined with Dihydroquercetin (taxifolin) also encompasses physiologically//nutraceutically/pharmaceutically acceptable salts and esters.

Examples of references that deal with the extraction of Arabinogalactan combined with Dihydroquercetin (taxifolin) from coniferous wood or the wood is hardwood are U.S. Pat. No. 5,756,098, EP Pat. No. 86608 which disclose a methods of extraction and/or purification of polysaccharide Arabinogalactan combined with Dihydroquercetin (taxifolin).

The daily oral dosage of Dihydroquercetin for humans (usually determined for a 70 kg person) is at least 100 mg. Preferably the daily dosage should be in the range of from about 1 mg/day to about 1000 mg/day, more preferably from about 5 mg/day to about 500 mg/day, most preferably from 10 to 100 mg/day.

The daily oral dosage of Arabinogalactan for humans (usually determined for a 70 kg person) is at least 10 g. Preferably the daily dosage should be in the range of from about 0.5 g/day to, about 1.5 g/day, more preferably from about 1 g/day to about 5 g/day, most preferably from 5 to 10 g/day.

The daily oral dosage for humans (usually determined for a 70 kg person) of Arabinogalactan combined with at least 1% up to 30% of Dihydroquerceting is at least 10 g. Preferably the daily dosage should be in the range of from about 0.3 g/day to about 15 g/day, more preferably from about 1 g/day to about 5 g/day, most preferably from 1 g/day to 3 g/day.

"The composition or preparation is administered orally to mammals, specifically humans" means that the composition is in any form that can be eaten or drunk by mammals or put into the stomach of mammals via the mouth/jaw.

In all embodiments of the invention, preferably the compositions or preparations are nutraceutical or phamaceutical, in particular nutraceutical compositions.

The term nutraceutical composition as used herein include food product, foodstuff, dietary supplement, nutritional supplement or a supplement composition for a food product or a foodstuff, preferably beverages (e.g. but not limited to sports beverages, functional waters, juices, smoothies; instant drinks), soups, dairy products (e.g. but not limited to single shot yogurt drinks), nutritional bars, and spreads, in particular beverages and nutritional bars.

As used herein, the term food product refers to any food or feed suitable for consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein the term foodstuff refers to any substance fit for human or animal consumption. The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term nutritional supplement refers to a composition comprising a dietary supplement in combination with a source of calories. In some embodiments, nutritional supplements are meal replacements or supplements (e.g., nutrient or energy bars or nutrient beverages or concentrates).

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat and fish products, cheese, yogurt and any other fat or oil containing foods, and food ingredients (e.g., wheat flour). The term food products or foodstuffs also includes functional foods and prepared food products, the latter referring to any pre-packaged food approved for human consumption.

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a powder, tablet or capsule and most preferably in the form of a hard (shell) gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methyl cellulose, povidone, carboxymethyl cellulose, coin starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the dietary supplement is provided as a powder or liquid suitable for adding by the consumer to a food or beverage, For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch). Sources of protein to be incorporated into the nutritional supplement of the invention can be any suitable protein utilized in nutritional formulations and can include whey protein, whey protein concentrate, whey powder, egg, soy flour, soy milk, soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; betacarotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; Vitamin E, inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein. It is understood by those of skill in the art that other ingredients can be added to those described herein, for example, fillers, emulsifiers, preservatives, etc. for the processing or manufacture of a nutritional supplement.

Additionally flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but, are not limited to, lecithin (e.g., from egg or soy), and/or mono- and diglycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate are used.

In addition to the carbohydrates described above, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of nutritional compounds Dihydroquercetin (taxifolin), Arabinogalactan and Arabinogalactan combined with Dihydroquercetin (taxifolin) administered via a nutraceutical composition will, of course, vary depending upon known factors, such as the physiological characteristics of the particular composition and its mode and route of administration; the age, health and weight of the recipient; the nature and extent of the symptoms; the kind of concurrent treatment; the frequency of intake; and the effect desired which can be determined by the expert in the field with normal trials/or with the usual considerations regarding the formulation of a nutraceutical composition.

A food or beverage suitably contains about 1 mg to about 1000 mg of Dihydroquercetin (taxifolin) per Serving and about 50 mg to 15000 mg of Arabinogalactan per serving and about 10 mg to 15000 mg of Arabinogalactan combined with Dihydroquercetin (taxifolin) per serving. If the composition is a pharmaceutical composition such a composition may contain Dihydroquercetin (taxifolin) in an amount from about 1 mg to about 2000 mg per dosage unit, e.g., per capsule or tablet, or from about 1 mg per daily dose to about 3000 mg per daily dose of a liquid formulation. If the composition is a pharmaceutical composition such a composition may contain Arabinogalactan in an amount from about 100 mg to about 15000 mg per dosage unit, e.g., per capsule or tablet, or from about 5000 mg per daily dose to about 15000 mg per daily dose of a liquid formulation. If the composition is a pharmaceutical composition such a composition may contain Arabinogalactan combined with Dihydroquercetin (taxifolin) in an amount from about 100 mg to about 15000 mg per dosage unit, e.g., per capsule or tablet, or from about 3000 mg per daily dose to about 15000 mg per daily dose of a liquid formulation.

The pharmaceutical compositions according to the invention preferably further comprise pharmaceutically acceptable carriers. Suitable pharmaceutical carriers are e.g. described in Remington's Pharmaceutical Sciences, supra, a standard reference text in this field. Examples of such pharmaceutically acceptable carriers are both inorganic and organic carrier materials, suitable for oral/parenteral/injectable administration and include water, gelatin, lactose, starch, magnesium stearate, talc, vegetable oils, and the like.

The pharmaceutical composition may further comprise conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The dosages and ratios of the individual components in a pharmaceutical composition can be determined by the expert in the field with normal preclinical and clinical trials, or with the usual considerations regarding the formulation of pharmaceutical composition.

In a preferred embodiment Dihydroquercetin (taxifolin) is administered via a pharmaceutical composition either in the form of a single dose or by multiple doses in an amount of at least 0.5 mg/kg bodyweight/day, preferably in an amount of 1-100 mg/kg body weight/day, most preferably in an amount of 4-50 mg/kg body weight/day.

In a preferred embodiment Arabinogalactan is administered via a pharmaceutical composition either in the form of a single dose or by multiple doses in an amount of at least 0.5 mg/kg bodyweight/day, preferably in an amount of 1-500 mg/kg body weight/day, most preferably in an amount of 5-300 mg/kg body weight/day.

In a preferred embodiment Arabinogalactan combined with Dihydroquercetin (taxifolin) is administered via a pharmaceutical composition either in the form of a single dose or by multiple doses in an amount of at least 0.5 mg/kg bodyweight/day, preferably in an amount of 1-300 mg/kg body weight/day, most preferably in an amount of 5-200 mg/kg body weight/day.

The compositions according to the present invention may be in any galenic form, that is suitable for administering to the animal body including the human body, more in particular in any form that is conventional for oral administration, e.g. in solid form, for example as (additives/supplements for) food or feed, food or feed premixes, fortified food or feed, tablets, pills, granules, dragees, capsules, and effervescent formulations such as powders and tablets, or in liquid form, for instance in the form of solutions, emulsions or suspensions, for example as beverages, pastes and oily suspensions. The pastes may be filed into hard or soft shell capsules, whereby the capsules feature e.g. a matrix of (fish, swine, poultry, cow) gelatin, plant proteins or ligninsulfonate. Examples for other application forms are forms for transdermal, parenteral, topical or injectable administration. The nutraceutical and pharmaceutical compositions may be in the form of controlled (delayed) release formulations. Examples of pharmaceutical compositions also include compositions suitable for topical application and transdermal absorption of the phenolic compound, such as cremes, gels, sprays, dry sticks, powders etc. In a preferred embodiment the compositions according to the invention are in the form of a tablet, a pill, a granule, a dragee, a capsule or an effervescent formulation.

The compositions according to the invention may also contain further active ingredients suitable for health care.

The preferred daily dosage of the subject composition as specified above may be administered in the form of one or more dosage units such as e.g. a tablet. Most preferably the daily dosage of the subject composition is provided in the form of one dosage unit taken twice daily, for a total of two dosage units a day, or in the form of two dosage units taken twice daily, for a total of four dosage units a day. Compared to taking the total daily dose once a day, twice daily dosing of half the total daily dose in one or more dosage units per dose provides improved absorption and better maintenance of blood levels of the essential ingredients.

Effective amount of nutritional compounds Dihydroquercetin (taxifolin), Arabinogalactan and Arabinogalactan combined with Dihydroquercetin (taxifolin) in these methods refers to an amount necessary to obtain a physiological effect. The physiological effect may be achieved by one single dose or by repeated doses. The dosage administered may, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired and can be adjusted by a person skilled in the art.

The invention will now be elucidated by way of the following examples, without however being limited thereto.

EXAMPLES

Example 1

A soft drink containing a nutritional compound Dihydroquercetin (taxifolin) may be prepares as follows:
A soft drink is prepared from the following ingredients:
water composition per 100 ml serving (calories—10 ccal.):
Purified potable water
Not flavored
Antioxidant—Dihydroquercetin (taxifolin)—from 2.0 mg up to 20 mg
Fructose/Glucose (4:1) mixture—4.5 g or sucralose and acesulfame potassium
Vitamins: niacin—1.0 mg, calcium pantotenat or lactate—0.33 mg, B6-0.11 mg, H-biotin—8.3 micro gram, caffeine—0.01.1 mg, B12—0.06 microgram.
Natural mineral complex (sodium, potassium—16.5 mg. magnesium—0.067 mg, chlorine 21.3 mg, sulfate—0.65 mg/100 ml, mineralization of no more than 0.95 g/dl)

Example 2

A soft drink containing a nutritional compound Dihydroquercetin (taxifolin) may be prepares as follows:
A soft drink is prepared from the following ingredients:
water composition per 100 ml serving:
Purified potable water
Natural flavor (Lemon Lime)
Fructose/Glucose (4:1) mixture—4 gr.
Larch Arabinogalactan combined with 5% of Dihydroquercetin (taxifolin) by dry weight—1 gr.
Vitamins: vitamin C—30 mg (ordinary form of fortification by manufacturer), niacin—1.0 mg/100 ml, calcium lactate—0.33 mg, B6-0.11 mg, H-biotin—8.3 micro gram, caffeine or folic acid—0.011 mg, B12—0.06 micro gram.
Calories per 100 mL—18 ccal.

The complete disclosures of the patents, patent documents, and publications cited herein are incorporated by reference in their entirety as if each were individually incorporated. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of using nutritional compounds for reducing and controlling cardiometabolic risk factors associated with a metabolic syndrome and a hypercholesterolemia in humans, the method comprising the steps of:
    identifying a particular human who has the metabolic syndrome by determining whether said particular human has at least three characteristics selected from the group consisting of:
    (a) a waist circumference greater than 102 cm for men and greater than 88 cm for women,
    (b) a triglyceride level greater than 150 mg/dl.
    (c) an HDL-cholesterol level less than 40 mg/dl for men and less than 50 mg/dl for women,
    (d) a blood pressure greater than or equal to 130/85 mmHG, and
    (e) a fasting glucose level greater than 110 mg/dl; and
    administering internally a nutritional compound comprising a combination of an Arabinogalactan and a Dihydroquercetin (taxifolin), said Arahinogalactan being present in said combination as a fiber matrix in an amount higher than 70% as determined by weight on a dry matter basis, and said Dihydroquercetin being present in said fiber matrix, such that, after said internal administration of said nutritional compound, said particular human has no more than one characteristic selected from the group consisting of (a), (b), (c), (d), and (e).

2. A method of using a nutritional compound comprising the steps of:
    manufacturing said nutritional compound to include a combination of an Arabinogalactan and a Dihydroquercetin (taxifolin) said Arabinogalactan being present in said combination as a fiber matrix in an amount higher than 70% as determined by weight on a dry matter basis, and said Dihydroquercetin being present in said fiber matrix;
    administering internally said nutritional compound to a human who suffers from a poor diet so as to provide support in said human in reducing, and controlling detrimental effects caused by the poor diet, wherein said controlling of the detrimental effects is selected from the group consisting of increase of short-chain fatty acids, decrease of colonic ammonia levels, increase of a number of beneficial bacteria in a colon, and improvement of an immune response.

3. A method of using a nutritional compound comprising the steps of:
    manufacturing said nutritional compound to include a combination of an Arabinogalactan and a Dihydroquercetin (taxifolin) said Arabinogalactan being present in said combination as a fiber matrix in an amount higher than 70% as determined by weight on a dry matter basis, and said Dihydroquercetin being present in said fiber matrix;
    administering internally said nutritional compound to a human who suffers from an abnormal inhibitory and excitatory neuron function so as to normalize the inhibitory and excitatory neuron function in said human.

4. A method of treating cardiometabolic disorders comprising the steps of:
    manufacturing a composition comprising a combination of an Arabinogalactan with a Dihydroquercetin (taxifolin) wherein said Arabinogalactan is present in said combination as a fiber matrix in an amount higher than 70% as determined by weight on a dry matter basis, wherein said Dihydroquercetin is present in said fiber matrix; and internally administering said composition to a mammal with a cardiometabolic disorder.

5. The method according to claim 4, wherein the cardiometabolic disorders are cardiovascular and metabolic syndrome disorders.

6. The method according to claim 4, wherein the composition is a nutraceutical composition.

7. The method according to claim 4, wherein the composition is a beverage.

8. The method according to claim 4, wherein the composition is in a form of a tablet, a pill, a granule, a dragee, a capsule or an effervescent formulation.

9. The method according to claim 4, wherein the composition is a nutrition bar.

10. The method according to claim 4, wherein one gram of said Arabinogalactan has a capacity to inhibit lipid oxidation equivalent to at least 1,000 umol Trolox Equivalent (TE) /gram based on an Oxygen Radical Absorbance Capacity (ORAC) value, wherein one gram of said arabinogalactan has an antioxidant capacity of Cell-based Antioxidant Protection (CAP-e) to protect live cells from oxidative damage to, at least 6 CAP-e units per gram, where the CAP-e value is in Gallic Acid Equivalent (GAE) units; and wherein said antioxidant capacity is derived from natural constituents of said combination of said arabinogalactan and said dihydroquercetin but not from added antioxidants.

11. The method according to claim 1, wherein one gram of said Arabinogalactan has a capacity to inhibit lipid oxidation equivalent to at least 1,000 umol Trolox Equivalent (TE) /gram based on an Oxygen Radical Absorbance Capacity (ORAC) value, wherein one gram of said arabinogalactan has an antioxidant capacity of Cell-based Antioxidant Protection (CAP-e) to protect live cells from oxidative damage to, at least 6 CAP-e units per gram, where the CAP-e value is in Gallic Acid Equivalent (GAE) units; and wherein said antioxidant capacity is derived from natural constituents of said combination of said arabinogalactan and said dihydroquercetin but not from added antioxidants.

* * * * *